(12) United States Patent
Bruns et al.

(10) Patent No.: US 11,696,781 B2
(45) Date of Patent: Jul. 11, 2023

(54) BLADE COOLING GAS/FLUID STORAGE

(71) Applicant: Cilag GmbH International, Zug (CH)

(72) Inventors: Jeffery D. Bruns, Cincinnati, OH (US); Ellen Burkart, Cincinnati, OH (US); Demetrius N. Harris, Cincinnati, OH (US); Troy Q. Le, West Chester, OH (US); Guion Y. Lucas, Cincinnati, OH (US); Alexander S. O'Leary, St. Charles, MO (US); Rafael J. Ruiz Ortiz, Mason, OH (US); Amrita S. Sawhney, Cincinnati, OH (US); Laura S. Downing, Cincinnati, OH (US); Christopher Q. Seow, Cincinnati, OH (US); Jeffrey C. Souder, Lexington, KY (US)

(73) Assignee: Cilag GmbH International, Zug (CH)

( * ) Notice: Subject to any disclaimer, the term of this patent is extended or adjusted under 35 U.S.C. 154(b) by 0 days.

(21) Appl. No.: 17/384,848

(22) Filed: Jul. 26, 2021

(65) Prior Publication Data
US 2022/0015797 A1    Jan. 20, 2022

Related U.S. Application Data

(63) Continuation of application No. 16/398,632, filed on Apr. 30, 2019, now Pat. No. 11,202,650.

(51) Int. Cl.
*A61B 17/32* (2006.01)
*A61B 17/00* (2006.01)

(52) U.S. Cl.
CPC ............ *A61B 17/320092* (2013.01); *A61B 2017/00367* (2013.01); *A61B 2017/00402* (2013.01);

(Continued)

(58) Field of Classification Search
CPC ...... A61B 2217/007; A61B 17/320092; A61B 2017/320074; A61B 2017/320095;
(Continued)

(56) References Cited

U.S. PATENT DOCUMENTS

| 5,322,055 A | 6/1994 | Davison et al. |
| 5,324,299 A | 6/1994 | Davison et al. |

(Continued)

FOREIGN PATENT DOCUMENTS

EP    1946708 B1    6/2011

OTHER PUBLICATIONS

International Search Report and Written Opinion dated Jun. 17, 2020, for International Application No. PCT/IB2020/053473, 8 pages.

(Continued)

*Primary Examiner* — Wade Miles
*Assistant Examiner* — Bridget E. Rabaglia
(74) *Attorney, Agent, or Firm* — Frost Brown Todd LLP

(57) ABSTRACT

A surgical instrument includes a body, a shaft assembly, an end effector, a clamp actuator, and a blade cooling system. The end effector has a clamp arm and an ultrasonic blade coupled with an ultrasonic transducer. The clamp arm is configured to selectively move from a first actuator position toward a second actuator position thereby directing movement of the clamp arm from the open position toward the closed position, respectively. The cooling system is operable to deliver fluid coolant to the ultrasonic blade to thereby cool the ultrasonic blade while the clamp actuator remains in the first actuator position.

20 Claims, 20 Drawing Sheets

(52) U.S. Cl.
CPC ............ *A61B 2017/320074* (2017.08); *A61B 2017/320094* (2017.08); *A61B 2017/320095* (2017.08); *A61B 2217/007* (2013.01)

(58) Field of Classification Search
CPC ........... A61B 2017/00367; A61B 2017/00402; A61B 2017/2929; A61B 2218/001; A61B 2218/002; A61B 17/320068; A61B 17/32; A61B 2017/320093; A61B 2017/320072; A61B 2017/22014; A61B 2017/320084; A61B 2018/00005; A61B 2018/00011; A61B 2017/320073; A61B 2017/320071; A61B 2017/32007; A61B 2017/320069
USPC ........................................................ 606/169
See application file for complete search history.

(56) References Cited

U.S. PATENT DOCUMENTS

| | | | |
|---|---|---|---|
| 5,776,155 | A | 7/1998 | Beaupre et al. |
| 5,873,873 | A | 2/1999 | Smith et al. |
| 5,938,633 | A | 8/1999 | Beaupre |
| 5,980,510 | A | 11/1999 | Tsonton et al. |
| 6,283,981 | B1 | 9/2001 | Beaupre |
| 6,309,400 | B2 | 10/2001 | Beaupre |
| 6,325,811 | B1 | 12/2001 | Messerly |
| 6,423,082 | B1 | 7/2002 | Houser et al. |
| 6,500,176 | B1 | 12/2002 | Truckai et al. |
| 6,773,444 | B2 | 8/2004 | Messerly |
| 6,783,524 | B2 | 8/2004 | Anderson et al. |
| 7,112,201 | B2 | 9/2006 | Truckai et al. |
| 7,125,409 | B2 | 10/2006 | Truckai et al. |
| 7,169,146 | B2 | 1/2007 | Truckai et al. |
| 7,186,253 | B2 | 3/2007 | Truckai et al. |
| 7,189,233 | B2 | 3/2007 | Truckai et al. |
| 7,220,951 | B2 | 5/2007 | Truckai et al. |
| 7,309,849 | B2 | 12/2007 | Truckai et al. |
| 7,311,709 | B2 | 12/2007 | Truckai et al. |
| 7,354,440 | B2 | 4/2008 | Truckal et al. |
| 7,381,209 | B2 | 6/2008 | Truckai et al. |
| 7,544,200 | B2 | 6/2009 | Houser |
| 8,057,498 | B2 | 11/2011 | Robertson |
| 8,461,744 | B2 | 6/2013 | Wiener et al. |
| 8,591,459 | B2 | 11/2013 | Clymer et al. |
| 8,591,536 | B2 | 11/2013 | Robertson |
| 8,623,027 | B2 | 1/2014 | Price et al. |
| 8,663,220 | B2 | 3/2014 | Wiener et al. |
| 8,911,460 | B2 | 12/2014 | Neurohr et al. |
| 8,986,302 | B2 | 3/2015 | Aldridge et al. |
| 9,023,071 | B2 | 5/2015 | Miller et al. |
| 9,095,367 | B2 | 8/2015 | Olson et al. |
| 9,113,943 | B2 | 8/2015 | Ross et al. |
| 9,381,058 | B2 | 7/2016 | Houser et al. |
| 9,393,037 | B2 | 7/2016 | Olson et al. |
| 9,795,379 | B2 | 10/2017 | Leimbach et al. |
| 9,949,785 | B2 | 4/2018 | Price et al. |
| 10,034,685 | B2 | 7/2018 | Boudreaux et al. |
| 10,172,636 | B2 | 1/2019 | Stulen et al. |
| 10,206,705 | B2 | 2/2019 | Estera et al. |
| 10,327,797 | B2 | 6/2019 | Conlon et al. |
| 10,492,820 | B2 | 12/2019 | Hibner et al. |
| 11,202,650 | B2 | 12/2021 | Bruns et al. |
| 2006/0079874 | A1 | 4/2006 | Faller et al. |
| 2007/0191713 | A1 | 8/2007 | Eichmann et al. |
| 2007/0282333 | A1 | 12/2007 | Fortson et al. |
| 2008/0200940 | A1 | 8/2008 | Eichmann et al. |
| 2009/0105750 | A1 | 4/2009 | Price et al. |
| 2011/0015660 | A1 | 1/2011 | Wiener et al. |
| 2012/0116265 | A1 | 5/2012 | Houser et al. |
| 2015/0080924 | A1 | 3/2015 | Stulen et al. |
| 2015/0141981 | A1 | 5/2015 | Price et al. |
| 2016/0143657 | A1 | 5/2016 | Estera et al. |
| 2016/0143658 | A1* | 5/2016 | Stokes ........... A61B 17/320092 606/169 |
| 2016/0143659 | A1 | 5/2016 | Glutz et al. |
| 2019/0000499 | A1 | 1/2019 | Stokes et al. |

OTHER PUBLICATIONS

U.S. Appl. No. 61/410,603, entitled "Energy-Based Surgical Instruments," filed Nov. 5, 2010.

* cited by examiner

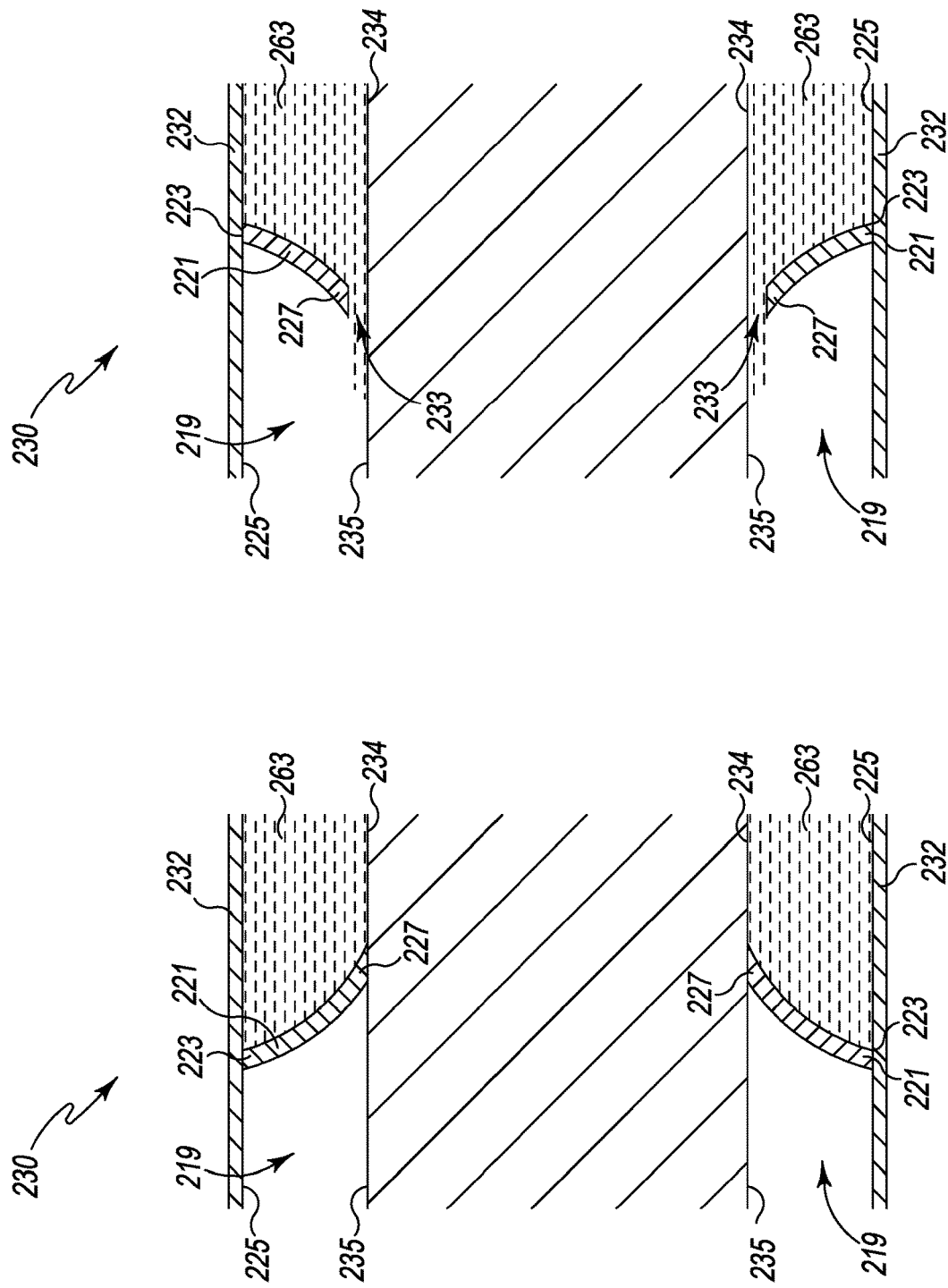

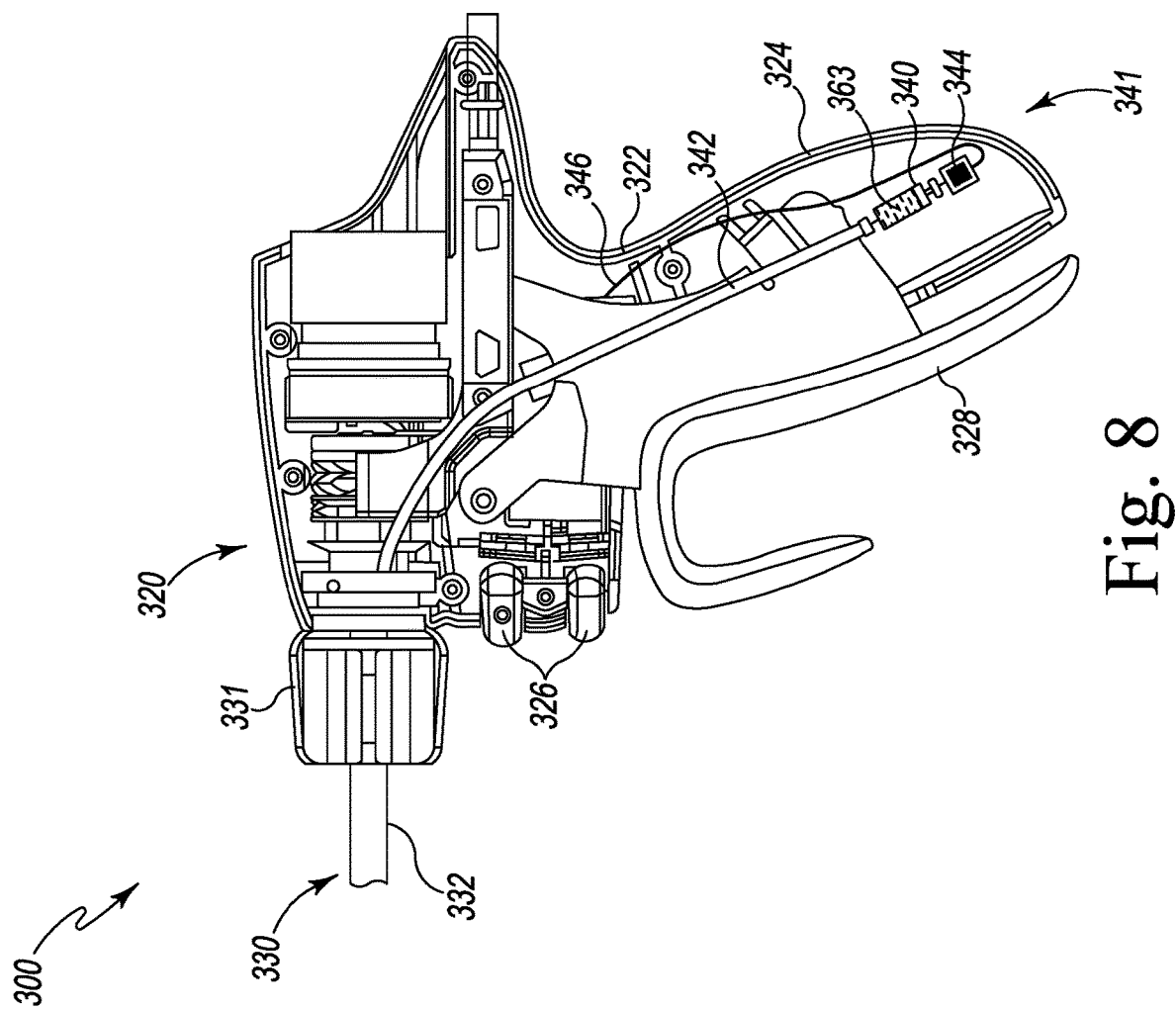

BLADE COOLING GAS/FLUID STORAGE

PRIORITY

This application is a continuation of U.S. patent application Ser. No. 16/398,632, entitled "Blade Cooling Gas/Fluid Storage," filed Apr. 30, 2019, issued as U.S. Pat. No. 11,202,650, on Dec. 21, 2021.

BACKGROUND

A variety of surgical instruments include an end effector having a blade element that vibrates at ultrasonic frequencies to cut and/or seal tissue (e.g., by denaturing proteins in tissue cells). These instruments include one or more piezoelectric elements that convert electrical power into ultrasonic vibrations, which are communicated along an acoustic waveguide to the blade element. The precision of cutting and coagulation may be controlled by the operator's technique and adjusting the power level, blade edge angle, tissue traction, and blade pressure.

Examples of ultrasonic surgical instruments include the HARMONIC ACE® Ultrasonic Shears, the HARMONIC WAVE® Ultrasonic Shears, the HARMONIC FOCUS® Ultrasonic Shears, and the HARMONIC SYNERGY® Ultrasonic Blades, all by Ethicon Endo-Surgery, Inc. of Cincinnati, Ohio. Further examples of such devices and related concepts are disclosed in U.S. Pat. No. 5,322,055, entitled "Clamp Coagulator/Cutting System for Ultrasonic Surgical Instruments," issued Jun. 21, 1994, the disclosure of which is incorporated by reference herein; U.S. Pat. No. 5,873,873, entitled "Ultrasonic Clamp Coagulator Apparatus Having Improved Clamp Mechanism," issued Feb. 23, 1999, the disclosure of which is incorporated by reference herein; U.S. Pat. No. 5,980,510, entitled "Ultrasonic Clamp Coagulator Apparatus Having Improved Clamp Arm Pivot Mount," issued Nov. 9, 1999, the disclosure of which is incorporated by reference herein; U.S. Pat. No. 6,283,981, entitled "Method of Balancing Asymmetric Ultrasonic Surgical Blades," issued Sep. 4, 2001, the disclosure of which is incorporated by reference herein; U.S. Pat. No. 6,309,400, entitled "Curved Ultrasonic Blade having a Trapezoidal Cross Section," issued Oct. 30, 2001, the disclosure of which is incorporated by reference herein; U.S. Pat. No. 6,325,811, entitled "Blades with Functional Balance Asymmetries for use with Ultrasonic Surgical Instruments," issued Dec. 4, 2001, the disclosure of which is incorporated by reference herein; U.S. Pat. No. 6,423,082, entitled "Ultrasonic Surgical Blade with Improved Cutting and Coagulation Features," issued Jul. 23, 2002, the disclosure of which is incorporated by reference herein; U.S. Pat. No. 6,773,444, entitled "Blades with Functional Balance Asymmetries for Use with Ultrasonic Surgical Instruments," issued Aug. 10, 2004, the disclosure of which is incorporated by reference herein; U.S. Pat. No. 6,783,524, entitled "Robotic Surgical Tool with Ultrasound Cauterizing and Cutting Instrument," issued Aug. 31, 2004, the disclosure of which is incorporated by reference herein; U.S. Pat. No. 8,057,498, entitled "Ultrasonic Surgical Instrument Blades," issued Nov. 15, 2011, the disclosure of which is incorporated by reference herein; U.S. Pat. No. 8,461,744, entitled "Rotating Transducer Mount for Ultrasonic Surgical Instruments," issued Jun. 11, 2013, the disclosure of which is incorporated by reference herein; U.S. Pat. No. 8,591,536, entitled "Ultrasonic Surgical Instrument Blades," issued Nov. 26, 2013, the disclosure of which is incorporated by reference herein; and U.S. Pat. No. 8,623,027, entitled "Ergonomic Surgical Instruments," issued Jan. 7, 2014, the disclosure of which is incorporated by reference herein.

Still further examples of ultrasonic surgical instruments are disclosed in U.S. Pub. No. 2006/0079874, entitled "Tissue Pad for Use with an Ultrasonic Surgical Instrument," published Apr. 13, 2006, now abandoned, the disclosure of which is incorporated by reference herein; U.S. Pub. No. 2007/0191713, entitled "Ultrasonic Device for Cutting and Coagulating," published Aug. 16, 2007, now abandoned, the disclosure of which is incorporated by reference herein; U.S. Pub. No. 2007/0282333, entitled "Ultrasonic Waveguide and Blade," published Dec. 6, 2007, now abandoned, the disclosure of which is incorporated by reference herein; U.S. Pub. No. 2008/0200940, entitled "Ultrasonic Device for Cutting and Coagulating," published Aug. 21, 2008, now abandoned, the disclosure of which is incorporated by reference herein; U.S. Pat. No. 8,911,460, entitled "Ultrasonic Surgical Instruments," issued Dec. 16, 2014, the disclosure of which is incorporated by reference herein; and U.S. Pat. No. 9,023,071, entitled "Ultrasonic Device for Fingertip Control," issued May 5, 2015, the disclosure of which is incorporated by reference herein.

Some ultrasonic surgical instruments may include a cordless transducer such as that disclosed in U.S. Pat. No. 9,381,058, entitled "Recharge System for Medical Devices," issued Jul. 5, 2016, the disclosure of which is incorporated by reference herein; U.S. Pub. No. 2012/0116265, entitled "Surgical Instrument with Charging Devices," published May 10, 2012, now abandoned, the disclosure of which is incorporated by reference herein; and/or U.S. Pat. App. No. 61/410,603, filed Nov. 5, 2010, entitled "Energy-Based Surgical Instruments," the disclosure of which is incorporated by reference herein.

Some ultrasonic surgical instruments may include an articulating shaft section. Examples of such ultrasonic surgical instruments are disclosed in U.S. Pat. No. 9,393,037, issued Jul. 19, 2016, entitled "Surgical Instruments with Articulating Shafts," the disclosure of which is incorporated by reference herein; and U.S. Pat. No. 9,095,367, issued Aug. 4, 2015, entitled "Flexible Harmonic Waveguides/Blades for Surgical Instruments," the disclosure of which is incorporated by reference herein.

Additionally, some ultrasonic surgical instruments may include an ultrasonic blade cooling system. Examples of such ultrasonic instruments are disclosed in U.S. Pub. No. 2019/0000499, entitled "Features to Drive Fluid Toward an Ultrasonic Blade of a Surgical Instrument," published Jan. 3, 2019, issued as U.S. Pat. No. 10,856,897 on Dec. 8, 2020, the disclosure of which is incorporated by reference herein; and U.S. Pub. No. 2016/0143659, entitled "Ultrasonic Surgical Instrument with Blade Cooling Through Retraction," published May 26, 2016, issued as U.S. Pat. No. 10,433,863 on Oct. 8, 2019, the disclosure of which is incorporated by reference herein.

While several surgical instruments and systems have been made and used, it is believed that no one prior to the inventors has made or used the invention described in the appended claims.

BRIEF DESCRIPTION OF THE DRAWINGS

While the specification concludes with claims which particularly point out and distinctly claim this technology, it is believed this technology will be better understood from the following description of certain examples taken in conjunction with the accompanying drawings, in which like reference numerals identify the same elements and in which:

FIG. 7A depicts an enlarged, cross-sectional side view of a one-way fluid valve of the shaft assembly of FIG. 4 taken along a centerline of the shaft assembly of FIG. 4 with the one-way fluid valve in a closed position;

FIG. 7B depicts the enlarged, cross-sectional side view of the one-way fluid valve of the shaft assembly similar to FIG. 7B, but showing the one-way fluid valve in an open position;

FIG. 8 depicts an enlarged, side elevational view of a fourth exemplary ultrasonic surgical instrument with a housing shroud removed for greater clarity;

Figure 1:
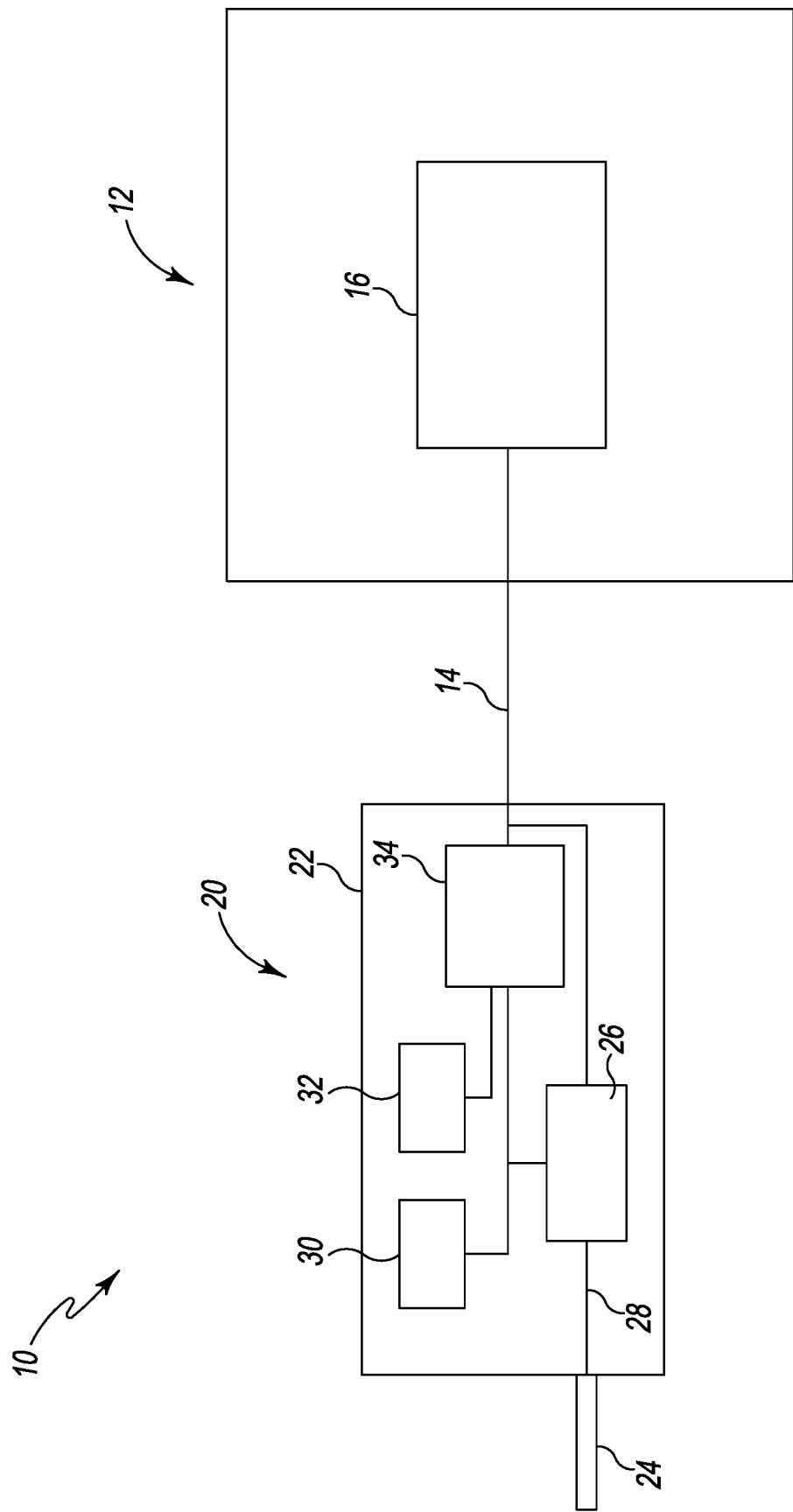
FIG. 1 depicts a diagrammatic view of an example of a surgical system including a first exemplary ultrasonic surgical instrument.

The drawings are not intended to be limiting in any way, and it is contemplated that various embodiments of the technology may be carried out in a variety of other ways, including those not necessarily shown in the drawings. The accompanying drawings incorporated in and forming a part of the specification illustrate several aspects of the present technology, and together with the description serve to explain the principles of the technology; it being understood, however, that this technology is not limited to the precise arrangements shown.

DETAILED DESCRIPTION

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

It is further understood that any one or more of the teachings, expressions, embodiments, examples, etc. described herein may be combined with any one or more of the other teachings, expressions, embodiments, examples, etc. that are described herein. The following-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

For clarity of disclosure, the terms "proximal" and "distal" are defined herein relative to an operator or other operator grasping a surgical instrument having a distal surgical end effector. The term "proximal" refers the position of an element closer to the operator or other operator and the term "distal" refers to the position of an element closer to the surgical end effector of the surgical instrument and further away from the operator or other operator.

I. OVERVIEW OF EXEMPLARY ULTRASONIC SURGICAL SYSTEM

FIG. 1 shows components of an example of a surgical system (10) in diagrammatic block form. As shown, system (10) comprises an ultrasonic generator (12) and a first exemplary ultrasonic surgical instrument (20). As will be described in greater detail below, instrument (20) is operable to cut tissue and seal or weld tissue (e.g., a blood vessel, etc.) substantially simultaneously, using ultrasonic vibrational energy. Generator (12) and instrument (20) are coupled together via cable (14). Cable (14) may comprise a plurality of wires; and may provide unidirectional electrical communication from generator (12) to instrument (20) and/or bidirectional electrical communication between generator (12) and instrument (20). By way of example only, cable (14) may comprise a "hot" wire for electrical power to surgical instrument (20), a ground wire, and a signal wire for transmitting signals from surgical instrument (20) to ultrasonic generator (12), with a shield surrounding the three wires. In some versions, separate "hot" wires are used for separate activation voltages (e.g., one "hot" wire for a first activation voltage and another "hot" wire for a second activation voltage, or a variable voltage between the wires proportional to the power requested, etc.). Of course, any other suitable number or configuration of wires may be used. It should also be understood that some versions of system (10) may incorporate generator (12) into instrument (20), such that cable (14) may simply be omitted.

By way of example only, generator (12) may comprise the GEN04, GEN11, or GEN 300 sold by Ethicon Endo-Surgery, Inc. of Cincinnati, Ohio. In addition, or in the alternative, generator (12) may be constructed in accordance with at least some of the teachings of U.S. Pat. No. 8,986,302, entitled "Surgical Generator for Ultrasonic and Electrosurgical Devices," issued Mar. 24, 2015, the disclosure of which is incorporated by reference herein. Alternatively, any other suitable generator (12) may be used. As will be described in greater detail below, generator (12) is operable to provide power to instrument (20) to perform ultrasonic surgical procedures.

Instrument (20) comprises a handpiece (22), which is configured to be grasped in one hand (or two hands) of an operator and manipulated by one hand (or two hands) of the operator during a surgical procedure. For instance, in some versions, handpiece (22) may be grasped like a pencil by the operator. In some other versions, handpiece (22) may include a scissor grip that may be grasped like scissors by the operator. In some other versions, handpiece (22) may include a pistol grip that may be grasped like a pistol by the operator. Of course, handpiece (22) may be configured to be gripped in any other suitable fashion. Furthermore, some versions of instrument (20) may substitute handpiece (22) with a body that is coupled to a robotic surgical system that is configured to operate instrument (20) (e.g., via remote control, etc.). In the present example, a blade (24) extends distally from the handpiece (22). Handpiece (22) includes an ultrasonic transducer (26) and an ultrasonic waveguide (28), which couples ultrasonic transducer (26) with blade (24). Ultrasonic transducer (26) receives electrical power from generator (12) via cable (14). By virtue of its piezoelectric properties, ultrasonic transducer (26) is operable to convert such electrical power into ultrasonic vibrational energy.

Ultrasonic waveguide (28) may be flexible, semi-flexible, rigid, or have any other suitable properties. As noted above, ultrasonic transducer (26) is integrally coupled with blade (24) via ultrasonic waveguide (28). Particularly, when ultrasonic transducer (26) is activated to vibrate at ultrasonic frequencies, such vibrations are communicated through ultrasonic waveguide (28) to blade (24), such that blade (24) will also vibrate at ultrasonic frequencies. When blade (24) is in an activated state (i.e., vibrating ultrasonically), blade (24) is operable to effectively cut through tissue and seal tissue. Ultrasonic transducer (26), ultrasonic waveguide (28), and blade (24) together thus form an acoustic assembly providing ultrasonic energy for surgical procedures when powered by generator (12). Handpiece (22) is configured to substantially isolate the operator from the vibrations of the acoustic assembly formed by transducer (26), ultrasonic waveguide (28), and blade (24).

In some versions, ultrasonic waveguide (28) may amplify the mechanical vibrations transmitted through ultrasonic waveguide (28) to blade (24). Ultrasonic waveguide (28) may further have features to control the gain of the longitudinal vibration along ultrasonic waveguide (28) and/or features to tune ultrasonic waveguide (28) to the resonant frequency of system (10). For instance, ultrasonic waveguide (28) may have any suitable cross-sectional dimensions/configurations, such as a substantially uniform cross-section, be tapered at various sections, be tapered along its entire length, or have any other suitable configuration. Ultrasonic waveguide (28) may, for example, have a length substantially equal to an integral number of one-half system wavelengths ($n\lambda/2$). Ultrasonic waveguide (28) and blade (24) may be fabricated from a solid core shaft constructed out of a material or combination of materials that propagates ultrasonic energy efficiently, such as titanium alloy (i.e., Ti-6Al-4V), aluminum alloys, sapphire, stainless steel, or any other acoustically compatible material or combination of materials.

In the present example, the distal end of blade (24) is located at a position corresponding to an anti-node associated with resonant ultrasonic vibrations communicated through waveguide (28) (i.e., at an acoustic anti-node), in order to tune the acoustic assembly to a preferred resonant frequency $f_{oo}$ when the acoustic assembly is not loaded by tissue. When transducer (26) is energized, the distal end of blade (24) is configured to move longitudinally in the range of, for example, approximately 10 to 500 microns peak-to-peak, and in some instances in the range of about 20 to about 200 microns at a predetermined vibratory frequency $f_o$ of, for example, 55.5 kHz. When transducer (26) of the present example is activated, these mechanical oscillations are transmitted through waveguide (28) to reach blade (24), thereby providing oscillation of blade (24) at the resonant ultrasonic frequency. Thus, the ultrasonic oscillation of blade (24) may simultaneously sever the tissue and denature the proteins in adjacent tissue cells, thereby providing a coagulative effect with relatively little thermal spread. In some versions, an electrical current may also be provided through blade (24) to also cauterize the tissue.

By way of example only, ultrasonic waveguide (28) and blade (24) may comprise components sold under product codes SNGHK and SNGCB by Ethicon Endo-Surgery, Inc. of Cincinnati, Ohio. By way of further example only, ultrasonic waveguide (28) and/or blade (24) may be constructed and operable in accordance with the teachings of U.S. Pat. No. 6,423,082, entitled "Ultrasonic Surgical Blade with Improved Cutting and Coagulation Features," issued Jul. 23, 2002, the disclosure of which is incorporated by reference herein. As another merely illustrative example, ultrasonic waveguide (28) and/or blade (24) may be constructed and operable in accordance with the teachings of U.S. Pat. No. 5,324,299, entitled "Ultrasonic Scalpel Blade and Methods of Application," issued Jun. 28, 1994, the disclosure of which is incorporated by reference herein. Other suitable properties and configurations of ultrasonic waveguide (28) and blade (24) will be apparent to those of ordinary skill in the art in view of the teachings herein.

Handpiece (22) of the present example also includes a control selector (30) and an activation switch (32), which are each in communication with a circuit board (34). By way of example only, circuit board (34) may comprise a conventional printed circuit board, a flex circuit, a rigid-flex circuit, or may have any other suitable configuration. Control selector (30) and activation switch (32) may be in communication with circuit board (34) via one or more wires, traces formed in a circuit board or flex circuit, and/or in any other suitable fashion. Circuit board (34) is coupled with cable (14), which is in turn coupled with control circuitry (16) within generator (12). Activation switch (32) is operable to selectively activate power to ultrasonic transducer (26). Particularly, when switch (32) is activated, such activation provides communication of appropriate power to ultrasonic transducer (26) via cable (14). By way of example only, activation switch (32) may be constructed in accordance with any of the teachings of the various references cited herein. Other various forms that activation switch (32) may take will be apparent to those of ordinary skill in the art in view of the teachings herein.

In the present example, surgical system (10) is operable to provide at least two different levels or types of ultrasonic energy (e.g., different frequencies and/or amplitudes, etc.) at blade (24). To that end, control selector (30) is operable to permit the operator to select a desired level/amplitude of ultrasonic energy. By way of example only, control selector (30) may be constructed in accordance with any of the teachings of the various references cited herein. Other various forms that control selector (30) may take will be apparent to those of ordinary skill in the art in view of the teachings herein. In some versions, when an operator makes a selection through control selector (30), the operator's selection is communicated back to control circuitry (16) of generator (12) via cable (14), and control circuitry (16) adjusts the power communicated from generator (12) accordingly the next time the operator actuates activation switch (32).

It should be understood that the level/amplitude of ultrasonic energy provided at blade (24) may be a function of characteristics of the electrical power communicated from generator (12) to instrument (20) via cable (14). Thus, control circuitry (16) of generator (12) may provide electrical power (via cable (14)) having characteristics associated with the ultrasonic energy level/amplitude or type selected through control selector (30). Generator (12) may thus be operable to communicate different types or degrees of electrical power to ultrasonic transducer (26), in accordance with selections made by the operator via control selector (30). In particular, and by way of example only, generator (12) may increase the voltage and/or current of the applied signal to increase the longitudinal amplitude of the acoustic assembly. As a merely illustrative example, generator (12) may provide selectability between a "level 1" and a "level 5," which may correspond with a blade (24) vibrational resonance amplitude of approximately 50 microns and approximately 90 microns, respectively. Various ways in which control circuitry (16) may be configured will be apparent to those of ordinary skill in the art in view of the teachings herein. It should also be understood that control selector (30) and activation switch (32) may be substituted with two or more activation switches (32). In some such versions, one activation switch (32) is operable to activate blade (24) at one power level/type while another activation switch (32) is operable to activate blade (24) at another power level/type, etc.

In some alternative versions, control circuitry (16) is located within handpiece (22). For instance, in some such versions, generator (12) only communicates one type of electrical power (e.g., just one voltage and/or current available) to handpiece (22), and control circuitry (16) within handpiece (22) is operable to modify the electrical power (e.g., the voltage of the electrical power), in accordance with selections made by the operator via control selector (30), before the electrical power reaches ultrasonic transducer (26). Furthermore, generator (12) may be incorporated into handpiece (22) along with all other components of surgical system (10). For instance, one or more batteries (not shown) or other portable sources of power may be provided in handpiece (22). Still other suitable ways in which the components shown in FIG. 1 may be rearranged or otherwise configured or modified will be apparent to those of ordinary skill in the art in view of the teachings herein.

II. OVERVIEW OF EXEMPLARY ULTRASONIC SURGICAL INSTRUMENT

The following discussion relates to various exemplary components and configurations that may be incorporated into one or more portions of instrument (20), discussed briefly above. It should be understood that the various examples of instrument (100) described below may be readily incorporated into surgical system (10) as described above. It should also be understood that the various components and operabilities of instrument (20) described above may be readily incorporated into the exemplary versions of instrument (100) described below. Various suitable ways in which the above and below teachings may be combined will be apparent to those of ordinary skill in the art in view of the teachings herein. It should also be understood that the below teachings may be readily combined with the various teachings of the references that are cited herein.

Figure 2:
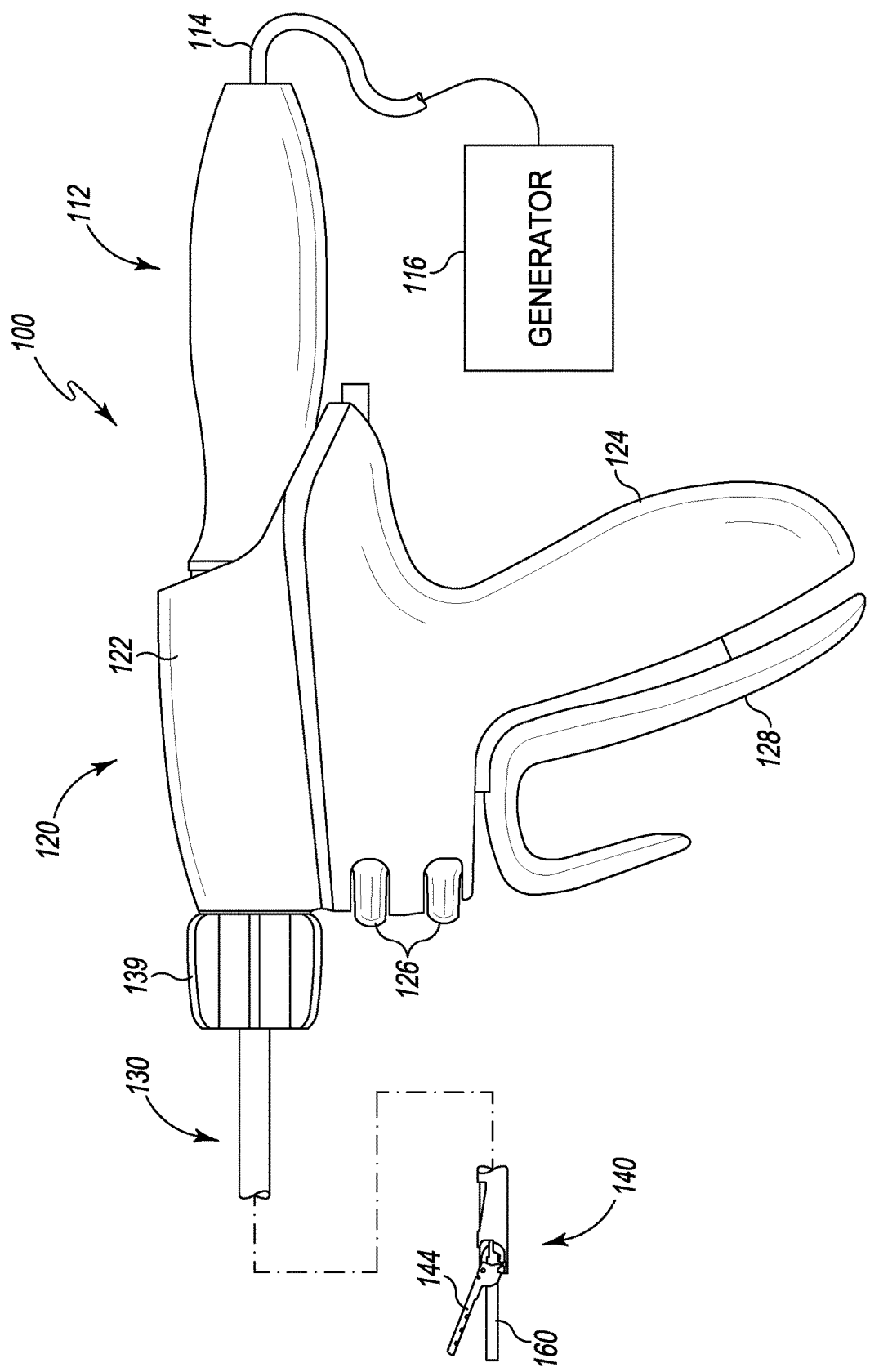
FIG. 2 depicts a side elevational view of a second exemplary ultrasonic surgical instrument.

To this end, FIG. 2 illustrates a second exemplary ultrasonic surgical instrument (100). At least part of instrument (100) may be constructed and operable in accordance with at least some of the teachings of U.S. Pat. Nos. 5,322,055; 5,873,873; 5,980,510; 6,325,811; 6,773,444; 6,783,524; 8,461,744; 8,623,027; U.S. Pub. No. 2006/0079874, now abandoned; U.S. Pub. No. 2007/0191713, now abandoned; U.S. Pub. No. 2007/0282333, now abandoned; U.S. Pub. No. 2008/0200940, now abandoned; U.S. Pat. Nos. 9,023,071; 9,381,058; U.S. Pub. No. 2012/0116265, now abandoned; U.S. Pub. No. 2019/0000499, issued as U.S. Pat. No. 10,856,897 on Dec. 8, 2020; U.S. Pub. No. 2016/0143659, issued as U.S. Pat. No. 10,433,863 on Oct. 8, 2019;U.S. Pat. Nos. 9,393,037; 9,095,367; U.S. Pat. App. No. 61/410,603; and/or U.S. Pat. No. 10,172,636. The disclosures of each of the foregoing patents, publications, and applications are incorporated by reference herein. As described therein and as will be described in greater detail below, instrument (100) is operable to cut tissue and seal or weld tissue (e.g., a blood vessel, etc.) substantially simultaneously. It should also be understood that instrument (100) may have various structural and functional similarities with the HARMONIC ACE® Ultrasonic Shears, the HARMONIC WAVE® Ultrasonic Shears, the HARMONIC FOCUS® Ultrasonic Shears, and/or the HARMONIC SYNERGY® Ultrasonic Blades. Furthermore, instrument (100) may have various structural and functional similarities with the devices taught in any of the other references that are cited and incorporated by reference herein.

To the extent that there is some degree of overlap between the teachings of the references cited herein, the HARMONIC ACE® Ultrasonic Shears, the HARMONIC WAVE® Ultrasonic Shears, the HARMONIC FOCUS® Ultrasonic Shears, and/or the HARMONIC SYNERGY® Ultrasonic Blades, and the following teachings relating to instrument (100), there is no intent for any of the description herein to be presumed as admitted prior art. Several teachings herein will in fact go beyond the scope of the teachings of the references cited herein and the HARMONIC ACE® Ultrasonic Shears, the HARMONIC WAVE® Ultrasonic Shears, the HARMONIC FOCUS® Ultrasonic Shears, and the HARMONIC SYNERGY® Ultrasonic Blades.

Instrument (100) of the present example comprises a body (122) which includes a handle assembly (120), a shaft assembly (130), and an end effector (140). Handle assembly (120) further includes a pistol grip (124) and a pair of buttons (126). Additionally, handle assembly (120) can include a trigger, or clamp actuator (128), that is pivotable toward and away from pistol grip (124). It should be understood, however, that various other suitable configurations may be used, including but not limited to a pencil-grip configuration or a scissor-grip configuration. End effector (140) includes an ultrasonic blade (160) and a pivoting clamp arm (144). Clamp arm (144) is coupled with clamp actuator (128) such that clamp arm (144) is pivotable toward ultrasonic blade (160) in response to pivoting of clamp actuator (128) toward pistol grip (124); and such that clamp arm (144) is pivotable away from ultrasonic blade (160) in response to pivoting of clamp actuator (128) away from, such as by releasing, pistol grip (124). Various suitable ways in which clamp arm (144) may be coupled with clamp actuator (128) will be apparent to those of ordinary skill in the art in view of the teachings herein.

An ultrasonic transducer assembly (112) extends proximally from body (122) of handle assembly (120). Transducer assembly (112) is coupled with a generator (116) via a cable (114). Transducer assembly (112) receives electrical power from generator (116) and converts that power into ultrasonic vibrations through piezoelectric principles. Generator (116) may include a power source and control module that is configured to provide a power profile to transducer assembly (112) that is particularly suited for the generation of ultrasonic vibrations through transducer assembly (112). By way of example only, generator (116) may comprise a GEN 300 sold by Ethicon Endo-Surgery, Inc. of Cincinnati, Ohio. In addition, or in the alternative, generator (116) may be constructed in accordance with at least some of the teachings of U.S. Pat. No. 8,986,302, entitled "Surgical Generator for Ultrasonic and Electrosurgical Devices," issued Mar. 24, 2015, the disclosure of which is incorporated by reference herein. It should also be understood that at least some of the functionality of generator (116) may be integrated into handle assembly (120), and that handle assembly (120) may even include a battery or other on-board power source such that cable (114) is omitted. Still other suitable forms that generator (116) may take, as well as various features and operabilities that generator (116) may provide, will be apparent to those of ordinary skill in the art in view of the teachings herein.

Figure 3:
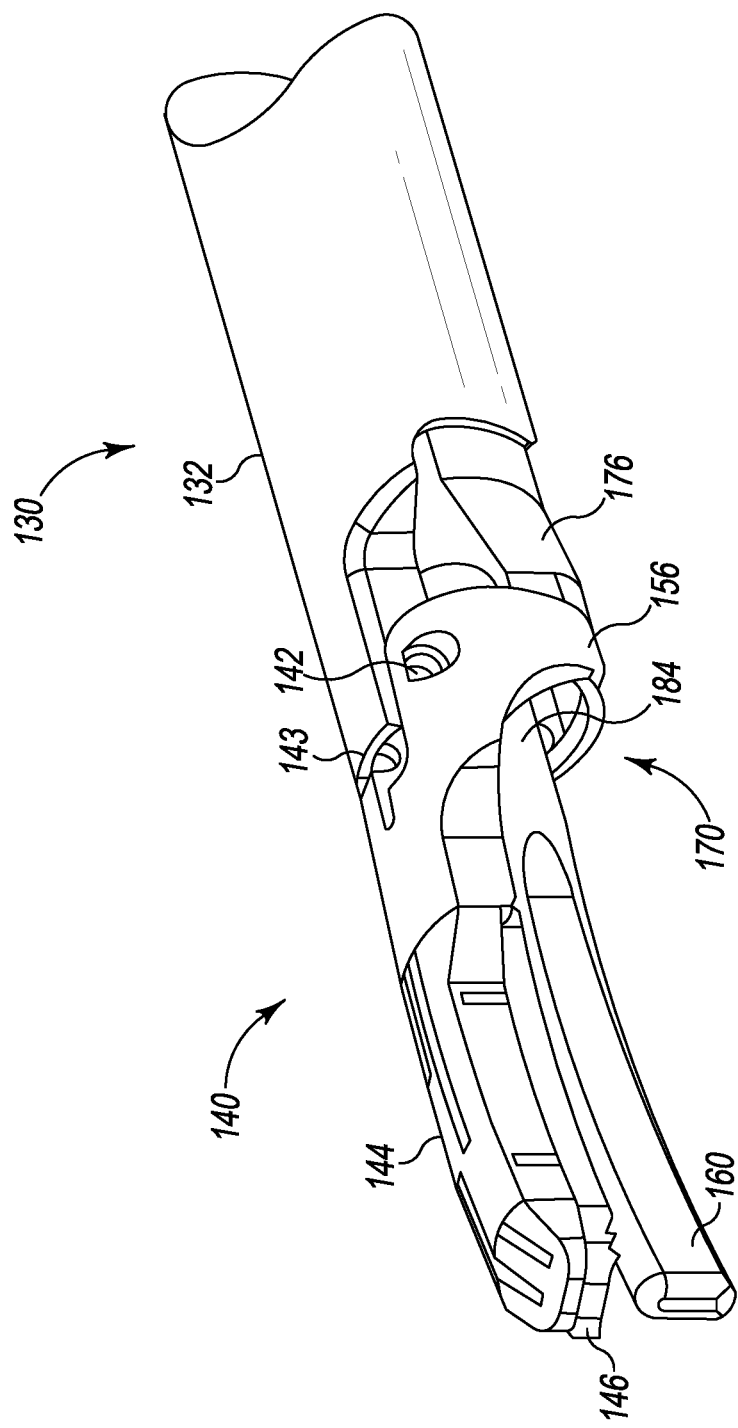
FIG. 3 depicts a perspective view of an end effector and a shaft assembly of the ultrasonic surgical instrument of FIG. 2.
Figure 4:
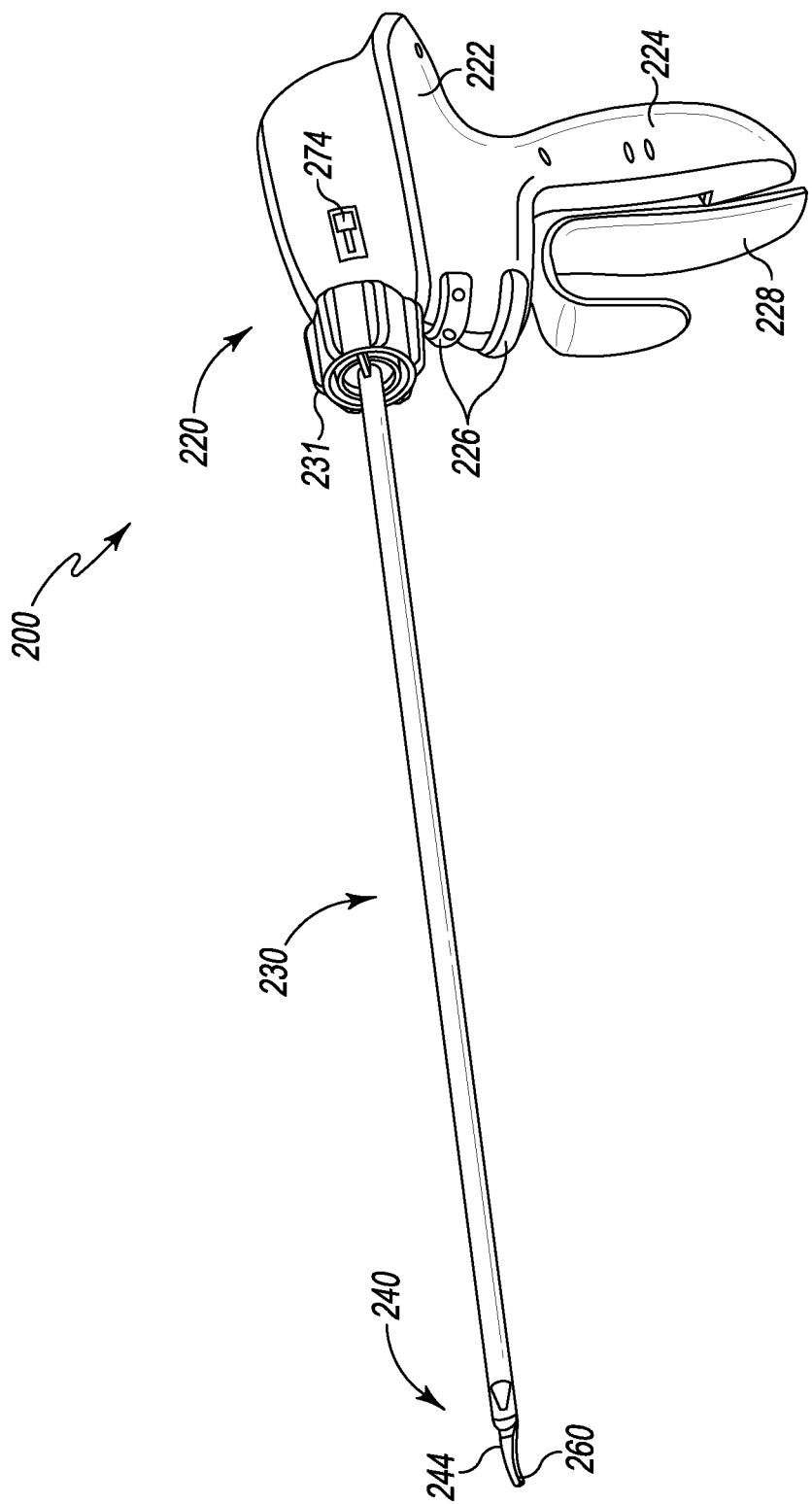
FIG. 4 depicts a perspective view of a third exemplary ultrasonic surgical instrument having a handle assembly, a shaft assembly, and an end effector.

With reference to FIG. 3, shaft assembly (130) of the present example comprises an outer sheath, such as outer tube (132), and an inner tube (176). Inner tube (176) is slidably disposed within outer tube (132). As will be discussed in more detail below, inner tube (176) is operable to translate longitudinally within outer tube (132) relative to outer tube (132) to selectively pivot clamp arm (144) toward and away from blade (160). Shaft assembly (130) of the present example further includes a rotation knob (139). Rotation knob (139) is operable to rotate the entire shaft assembly (130) and end effector (140) relative to handle assembly (120) about a longitudinal axis of shaft assembly (130). In some versions, rotation knob (139) is operable to selectively lock the angular position of shaft assembly (130) and end effector (140) relative to handle assembly (120) about the longitudinal axis of shaft assembly (130). For instance, rotation knob (139) may be translatable between a first longitudinal position, in which shaft assembly (130) and end effector (140) are rotatable relative to handle assembly (120) about the longitudinal axis of shaft assembly (130); and a second longitudinal position, in which shaft assembly (130) and end effector (140) are not rotatable relative to handle assembly (120) about the longitudinal axis of shaft assembly (130). Of course, shaft assembly (130) may have a variety of other components, features, and operabilities, in addition to or in lieu of any of those noted above. By way of example only, at least part of shaft assembly (130) may be constructed in accordance with at least some of the teachings of U.S. Pat. No. 9,795,379, entitled "Surgical Instrument with Multi-Diameter Shaft," issued Oct. 24, 2017, the disclosure of which is incorporated by reference herein. Other suitable configurations for shaft assembly (130) will be apparent to those of ordinary skill in the art in view of the teachings herein.

As best seen in FIG. 3, end effector (140) of the present example comprises clamp arm (144) and ultrasonic blade (160), with the ultrasonic blade (160) coupled to the acoustic waveguide (184). Clamp arm (144) includes a primary clamp pad (146) and a secondary clamp pad (not shown) that are secured to the underside of clamp arm (144), facing blade (160). Clamp arm (144) is pivotably secured to a distally projecting tongue (143) of outer tube (132) via a pin (142). Clamp arm (144) is operable to selectively pivot toward and away from blade (160) to selectively clamp tissue between clamp arm (144) and blade (160). A pair of arms (156) extend transversely from clamp arm (144) and are secured to a distal portion (170) of inner tube (176) that extends laterally between arms (156). Inner tube (176) is operable to translate longitudinally within outer tube (132) relative to outer tube (132) to selectively pivot clamp arm (144) toward and away from blade (160). In particular, inner tube (176) is coupled with clamp actuator (128) such that clamp arm (144) pivots toward blade (160) in response to pivoting of clamp actuator (128) toward pistol grip (124); and such that clamp arm (144) pivots away from blade (160) in response to pivoting of clamp actuator (128) away from pistol grip (124). Clamp arm (144) may be biased toward the open position, such that (at least in some instances) the operator may effectively open clamp arm (144) by releasing a grip on clamp actuator (128).

Blade (160) of the present example is operable to vibrate at ultrasonic frequencies in order to effectively cut through and seal tissue, particularly when the tissue is being clamped between clamp pad (146) and blade (160). Blade (160) is positioned at the distal end of an acoustic drivetrain, including transducer assembly (112) and acoustic waveguide (184). Transducer assembly (112) includes a set of piezoelectric discs (not shown) located proximal to a horn (not shown) of rigid acoustic waveguide (184). The piezoelectric discs are operable to convert electrical power into ultrasonic vibrations, which are then transmitted along acoustic waveguide (184) to blade (160) in accordance with known configurations and techniques. By way of example only, this portion of the acoustic drivetrain may be configured in accordance with various teachings of various references that are cited herein.

In the present example, the distal end of blade (160) is located at a position corresponding to an anti-node associated with resonant ultrasonic vibrations communicated through acoustic waveguide (184), in order to tune the acoustic assembly to a preferred resonant frequency $f_o$ when the acoustic assembly is not loaded by tissue. When transducer assembly (112) is energized, the distal end of blade (160) is configured to move longitudinally in the range of, for example, approximately 10 to 500 microns peak-to-peak, and in some instances in the range of about 20 to about 200 microns at a predetermined vibratory frequency $f_o$ of, for example, 55.5 kHz. When transducer assembly (112) of the present example is activated, these mechanical oscillations are transmitted through acoustic waveguide (184) to reach blade (160), thereby providing oscillation of blade (160) at the resonant ultrasonic frequency. Thus, when tissue is secured between blade (160) and clamp pad (146), the ultrasonic oscillation of blade (160) may simultaneously sever the tissue and denature the proteins in adjacent tissue cells, thereby providing a coagulative effect with relatively little thermal spread. In some versions, an electrical current may also be provided through blade (160) and clamp arm (144) to also cauterize the tissue. While some configurations for an acoustic transmission assembly and transducer assembly (112) have been described, still other suitable configurations for an acoustic transmission assembly and transducer assembly (112) will be apparent to one or ordinary skill in the art in view of the teachings herein. Similarly, other suitable configurations for end effector (140) will be apparent to those of ordinary skill in the art in view of the teachings herein.

III. EXEMPLARY ULTRASONIC SURGICAL INSTRUMENT WITH BLADE COOLING SYSTEM

In some instances, one or more regions of instrument (20, 100) may heat up during extended operation of instrument (20, 100) in a surgical procedure. By way of example only, blade (24, 160), clamp arm (144), and/or other portions of instrument (20, 100) may eventually heat up over time. Such heating may be caused by friction and/or other factors. To the extent that the heat is initially generated in one particular component of instrument (20, 100) (e.g., blade (24, 160) or clamp arm (144), etc.), such heat may be gradually transmitted to other portions of instrument (20, 100). It may be desirable to reduce such heating and/or otherwise manage such heating in order to avoid contacting tissue with heated portions of instrument (20, 100) in accordance with one or more preferences of the operator to improve patient outcomes. For instance, the operator may prefer end effector (140) to be relatively cooled when the operator uses end effector (140) to perform spreading blunt dissections and/or simple tissue grasping, etc. It may also be desirable to reduce heat and/or otherwise manage heat in a way that does not significantly increase the size or operability of instrument (20, 100).

One merely exemplary way in which heat may be managed in instrument (20, 100) is to use a fluid to cool blade (24, 160). For instance, a cooling fluid (e.g., liquid saline, etc.) may be applied to the proximal end of blade (24, 160). The cooling fluid may then be communicated distally along the rest of the length of blade (24, 160) to thereby cool blade (24, 160). Various examples of ultrasonic surgical instruments (200, 300, 400, 500) described below provide various structures and techniques through which a cooling fluid may be communicated to a blade, such as blade (24, 160). One or more portions of such cooling features associates with ultrasonic surgical instruments (200, 300, 400, 500), discussed below, may thus be incorporated, in whole or in part, in instrument (20, 100) as desired. While various examples of features configured to cool blade (24, 160) will be described in greater detail below, other examples will be apparent to those of ordinary skill in the art according to the teachings herein.

A. Exemplary Ultrasonic Surgical Instrument with Fluid Plunger

FIGS. 4-7B illustrate a third exemplary ultrasonic surgical instrument (200) with a blade cooling system (241) that is configured to operate substantially similar to instrument (100) discussed above except for the differences discussed below. It should therefore be understood that instrument (200) may include the same components and operabilities as instrument (20, 100), in addition to including the components and operabilities described below. Instrument (200) of the present example comprises a body (222) with a handle assembly (220), a shaft assembly (230), and an end effector (240).

As with instrument (100) discussed above, body (222) is configured to receive an ultrasonic transducer assembly (not shown). Handle assembly (220) of body (222) includes a pistol grip (224) and a pair of buttons (226). Handle assembly (220) also includes a trigger, or clamp actuator (228), that is pivotable toward and away from pistol grip (224). End effector (240) includes an ultrasonic blade (260) and a pivoting clamp arm (244). Clamp arm (244) is coupled with clamp actuator (228) such that clamp arm (244) is pivotable toward ultrasonic blade (260) in response to pivoting of clamp actuator (228) from the first actuator position (the biased or "home" position) to the second actuator position (clamped toward pistol grip (224)); and such that clamp arm (244) is pivotable away from ultrasonic blade (260) in response to pivoting of clamp actuator (228) away from pistol grip (224), such as by releasing clamp actuator (228) from the second actuator position back to the first actuator position. In some embodiments, one or more resilient members are used to bias clamp arm (244) and/or clamp actuator (228) to an open position.

Figure 5A:
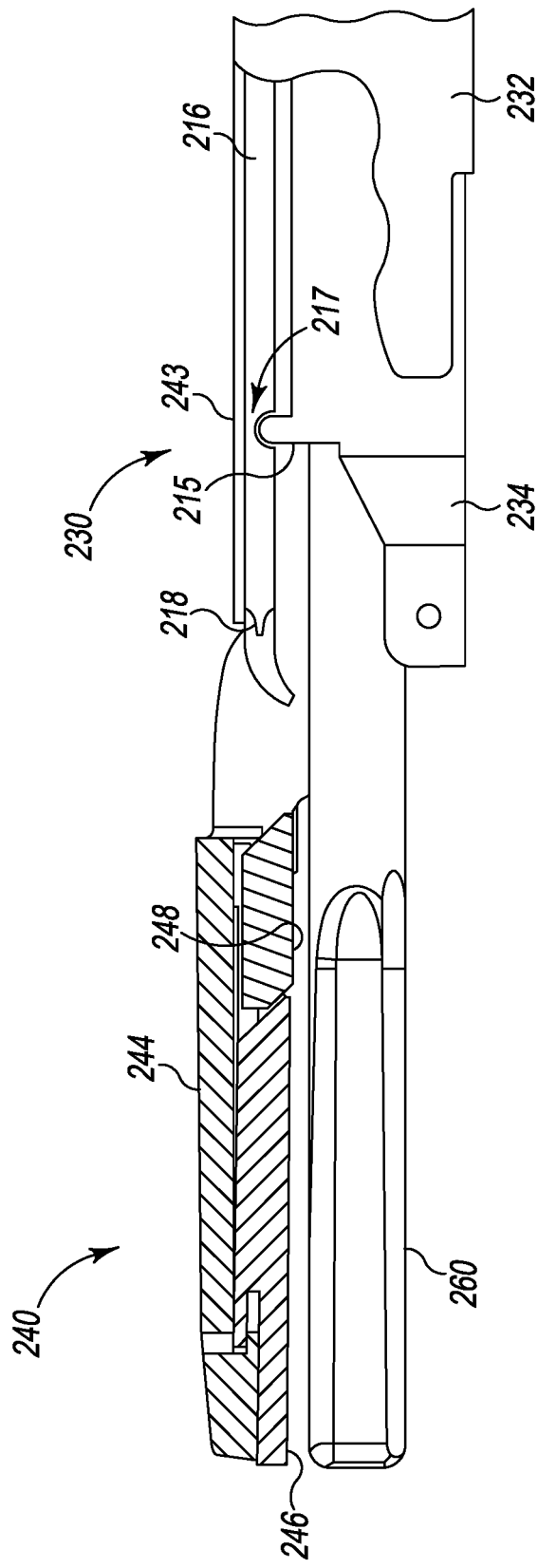
FIG. 5A depicts a cross-sectional side view of the end effector of FIG. 4 taken along a centerline thereof and in a closed position for compressing a tissue.

With respect to FIG. 5A, shaft assembly (230) of the present example comprises an outer sheath, or outer tube (232), and an inner tube (234). Inner tube (234) is slidably disposed within outer tube (232). As with shaft assembly (130) (see FIG. 3) discussed above, inner tube (234) is operable to translate longitudinally within outer tube (232) relative to outer tube (232) to selectively pivot clamp arm (244) toward and away from blade (260). End effector (240) of the present example comprises clamp arm (244) and ultrasonic blade (260). Clamp arm (244) includes a primary clamp pad (246) and a secondary clamp pad (248) that are secured to the underside of clamp arm (244), facing blade (260). Clamp arm (244) is pivotably secured to a distally projecting tongue (243) of outer tube (232) via a pin (not shown). Clamp arm (244) is operable to selectively pivot toward and away from blade (260) to selectively clamp tissue between clamp arm (244) and blade (260).

Figure 5B:
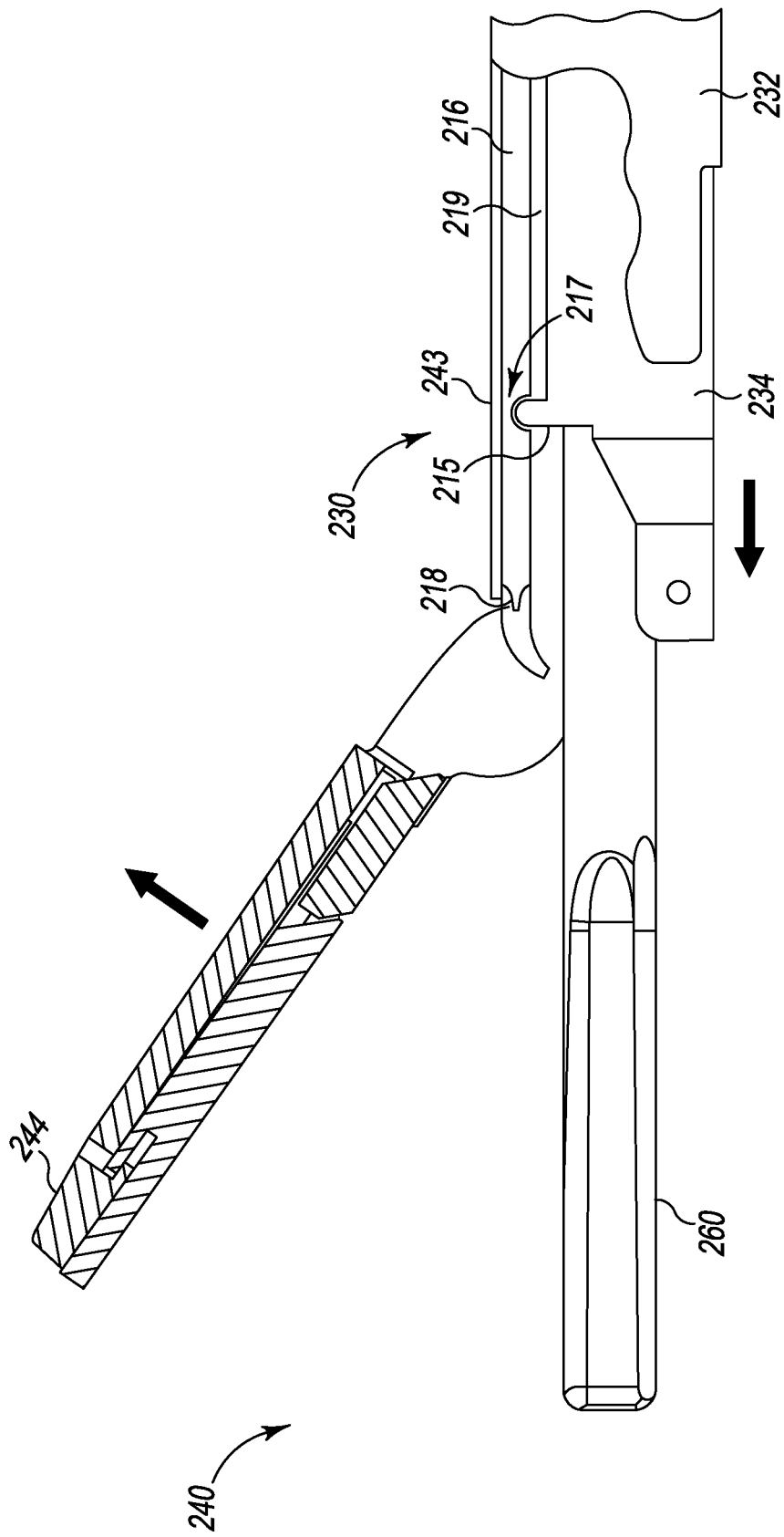
FIG. 5B depicts the cross-sectional side view the end effector similar to FIG. 5A, but with the end effector in an open position for receiving or releasing the tissue.

FIGS. 5A-5B illustrate the operation of clamp arm (244) between a closed position (FIG. 5A) and an open position (FIG. 5B). As shown in FIG. 5B, when inner tube (234) is in a distal position relative to outer tube (232), clamp arm (244) is in the open position. As shown in FIG. 5A, as inner tube (234) is moved proximally into an intermediate position, clamp arm (244) is pivoted toward blade (260) into an intermediate position. Exemplary end effector (240) and shaft assembly (230) are configured to provide fluid coolant to an ultrasonic blade (260). End effector (240) is configured to operate substantially similar to end effector (140) (see FIG. 3) discussed above except for the differences discussed below. It should therefore be understood that end effector (240) may be readily substituted for end effector (140) (see FIG. 3). Various suitable ways in which clamp arm (244) may be coupled with outer tube (232) and inner tube (234) will be apparent to those of ordinary skill in the art in view of the teachings herein.

In one example, shaft assembly (230) further comprises a tube (216) disposed between outer tube (232) and inner tube (234). Tube (216) is fluidly coupled to a fluid reservoir (for example, fluid reservoir (262) as shown in FIGS. 7A-7C) and is operable to provide fluid coolant from the fluid reservoir to ultrasonic blade (260) via tube (216) as will be described below in more detail. In one illustrative example, the proximal end of tube (216) may be closed by a one-way valve (218) that permits atmospheric air to be drawn into tube (216) yet inhibits fluid coolant from escaping the proximal end of tube (216), such that tube (216) may serve as its own fluid reservoir. Although one-way valve (218) of the present example is shown as a duckbill valve, one-way valve (218) may have any other suitable configuration as will be apparent to those of ordinary skill in the art in view of the teachings herein.

In this example, inner tube (234) comprises a projection (215) extending from a distal portion of inner tube (234). Tube (216) is disposed within shaft assembly (230) adjacent to projection (215) of inner tube (234) such that projection (215) bears against an exterior surface of tube (216) and causes tube (216) to deform as projection (215) translates with inner tube (234). While projection (215) bears into tube (216) and thereby deforms tube (216), projection (215) does not completely pinch tube (216) closed at the point where projection (215) engages tube (216). Instead, projection (215) is configured to leave a small gap (217) in the region where projection (215) engages tube. When inner tube (234) translates distally, projection (215) slides distally along tube (216), such that the deformation of inner tube (234) translates distally. This distal translation urges fluid coolant distally in inner tube (234) and out through one-way valve (218). It should be understood that the fluid coolant may travel distally and out through one-way valve (218) even though there is still a small gap (217) in the region where projection (215) engages tube (216). This is because one-way valve (218) provides less resistance to the flow of fluid coolant than the restriction at gap (217) provides. However, once inner tube (234) is retracted back proximally, fluid coolant will eventually flow distally through gap (217) to fill the region of tube (216) distal to gap (217), placing tube (216) in a state for subsequent dispensation of fluid coolant.

In an alternative example, shaft assembly (230) comprises a cavity (219) or void between the outer surface (235) of inner tube (234) and the inner surface (225) of outer tube (232). While this cavity (219) permits inner tube (234) and outer tube (232) to move relative to one another to actuate clamp arm (244), cavity (219) can also be utilized to direct fluid coolant (263) toward ultrasonic blade (260) such as by inserting fluid coolant (263) into cavity (219) at the proximal end and pressurizing it so it moves distally through shaft assembly (230) to exit at or near ultrasonic blade (260). In this configuration, tube (216) may not be required or, alternatively, may extend along some portion of shaft assembly (230) to fluidly connect with cavity (219).

Figure 6A:
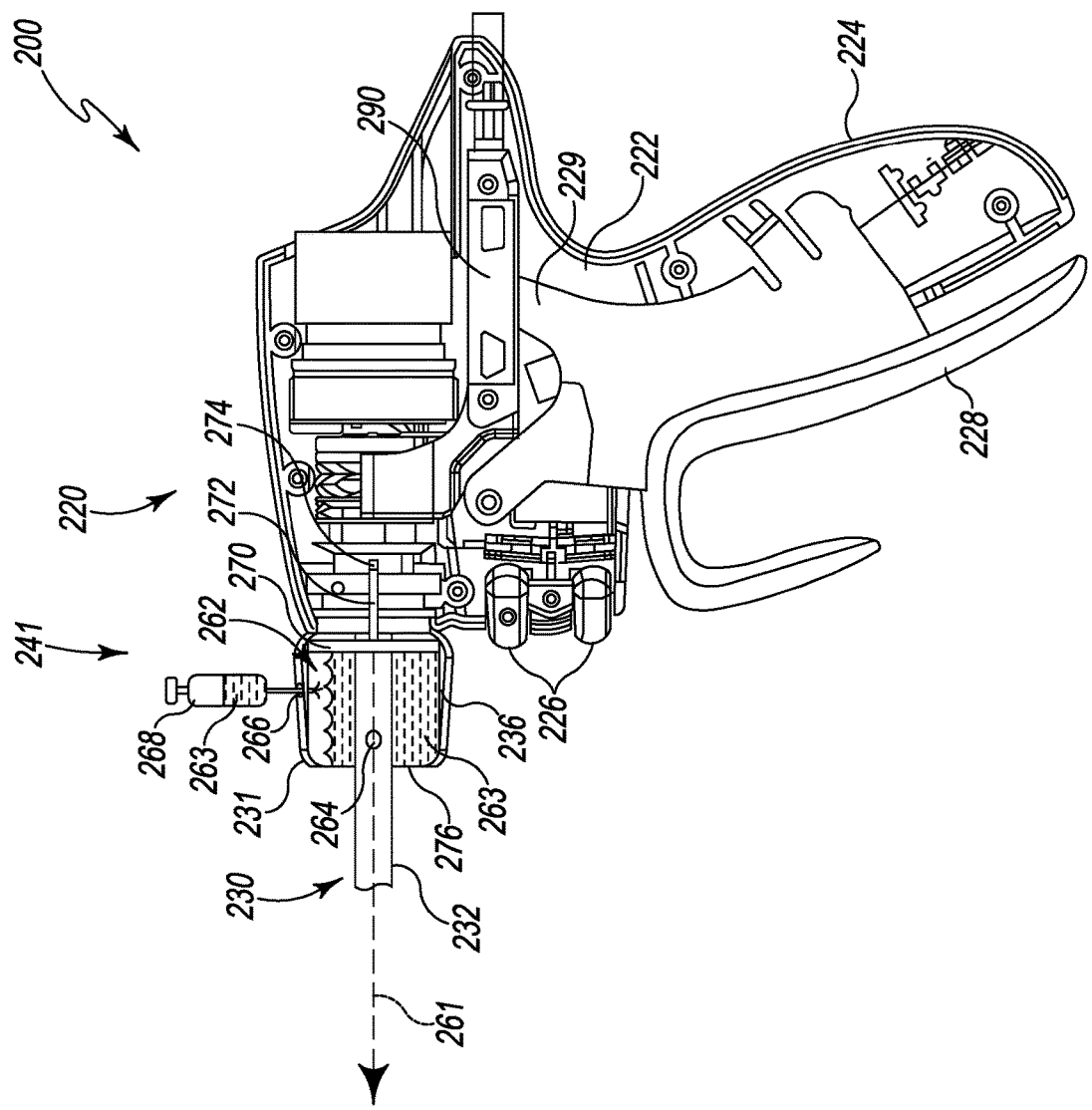
FIG. 6A depicts a side elevational view of the handle assembly of FIG. 4 with a housing shroud removed for greater clarity and a fluid reservoir being filled with fluid by a syringe.
Figure 6B:
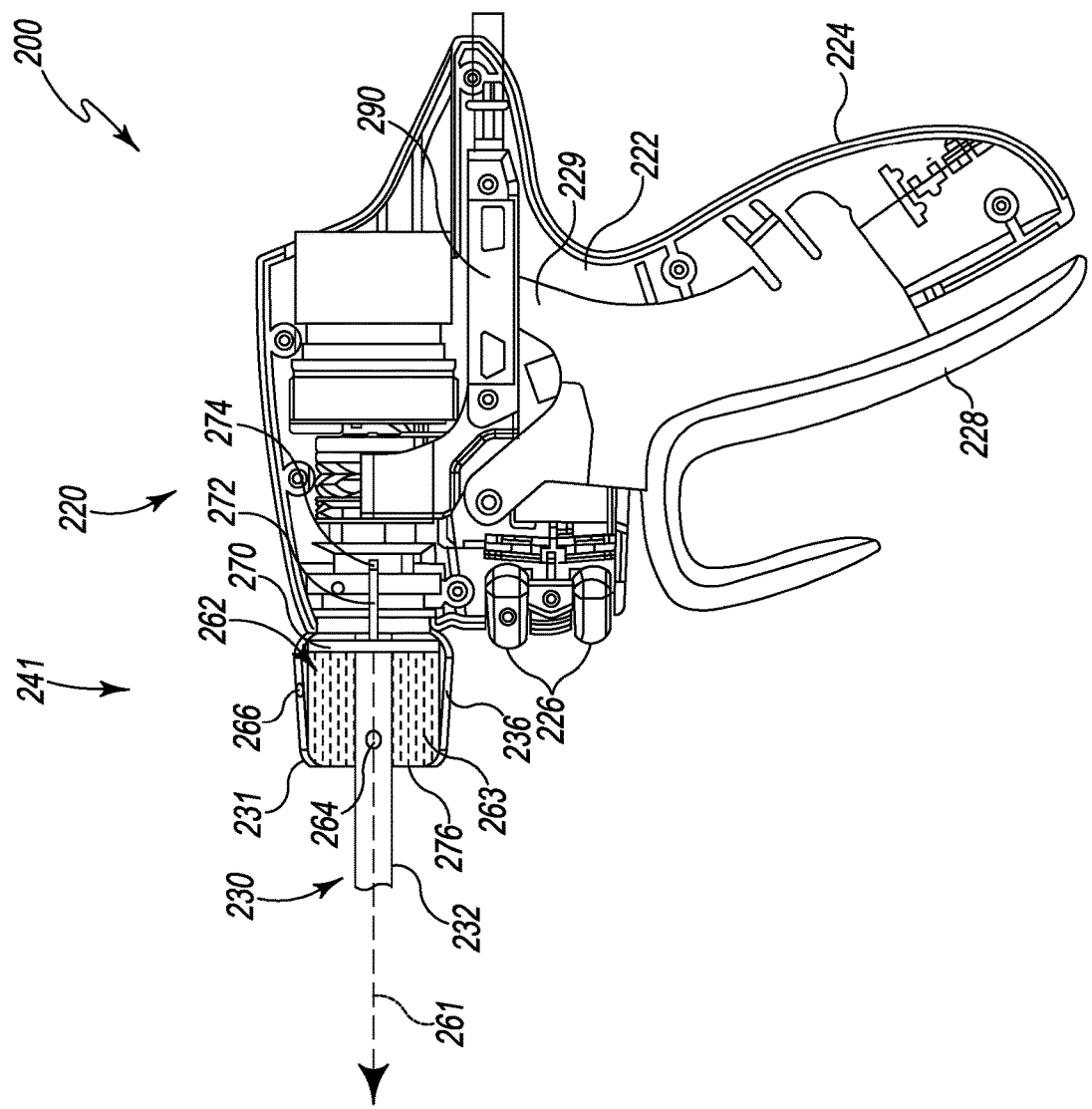
FIG. 6B depicts the side elevational view of the handle assembly similar to FIG. 6A, but showing the fluid reservoir filled with fluid.
Figure 6C:
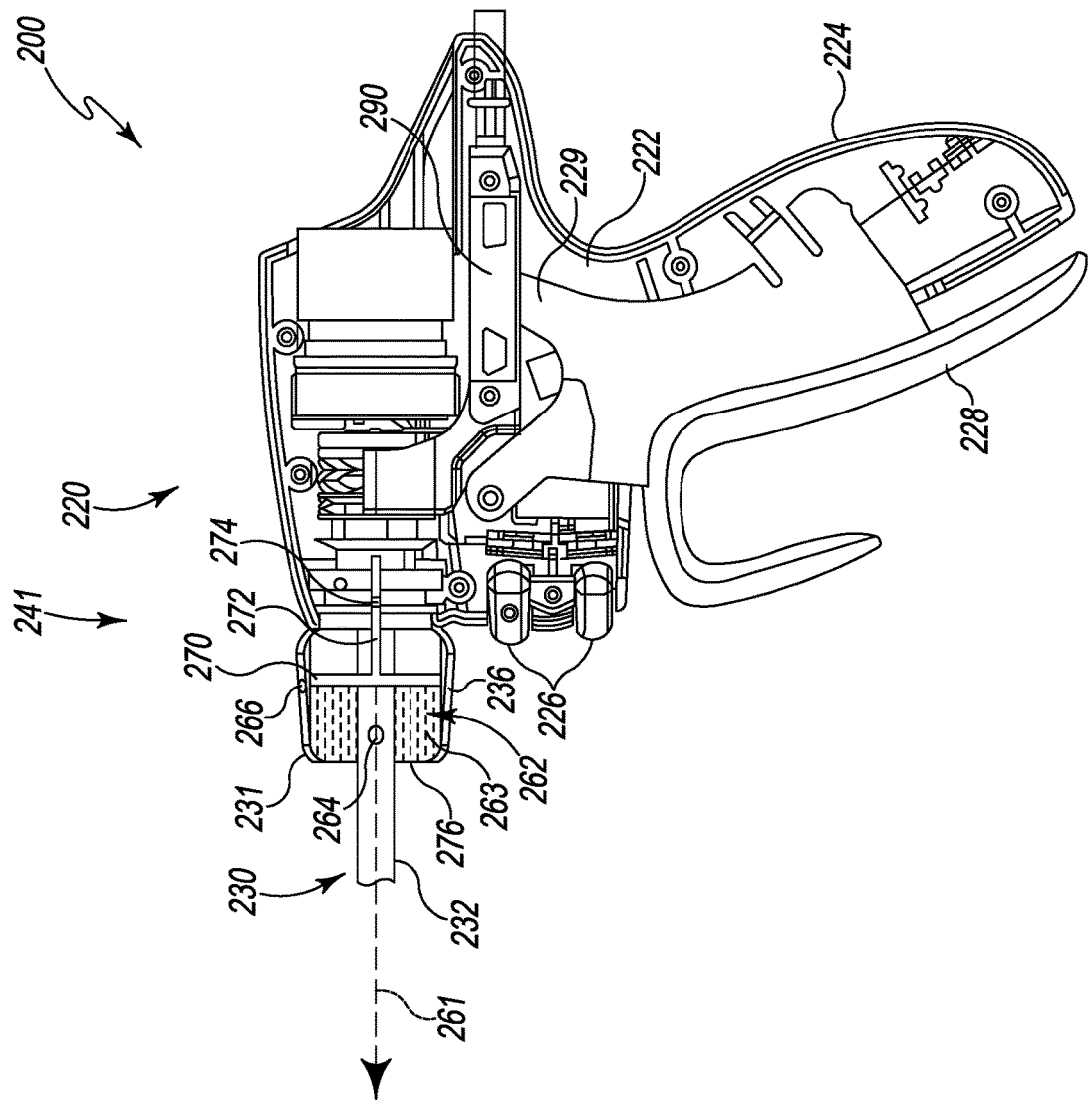
FIG. 6C depicts the side elevational view of the handle assembly similar to FIG. 6B, but showing fluid being discharged from the fluid reservoir.

FIGS. 6A-6C show interior components of handle assembly (220). Clamp actuator (228) is pivotably coupled to body (222) such that clamp actuator (228) is operable to pivot toward and away from pistol grip (224). Clamp actuator (228) is coupled with a yoke (290) via a linkage (229) such that rotation of clamp actuator (228) causes longitudinal translation of yoke (290). Yoke (290) is longitudinally translatable within body (222) between a proximal longitudinal position and a distal longitudinal position. Yoke (290) is supported by rails (not shown) formed in body (222), such that yoke (290) is constrained to longitudinal movement. Because the proximal portion of clamp actuator (228) is coupled with yoke (290) via linkage (229), it should be understood that pivoting of clamp actuator (228) toward pistol grip (224) will cause proximal longitudinal translation of yoke (290) within body (222); and that pivoting of clamp actuator (228) away from pistol grip (224) will cause distal longitudinal translation of yoke (290) within body (222). More particularly, pivoting of clamp actuator (228) away from pistol grip (224) causes distal longitudinal translation of yoke (290) within body (222) which in turn causes distal translation of inner tube (234), which in turn causes clamp arm (244) to pivot away from blade (260).

As discussed above, shaft assembly (230) comprises outer tube (232) and inner tube (234) (see FIG. 5A). Shaft assembly (230) of the present example further includes a rotation knob (231). Rotation knob (231) is operable to rotate an entirety of shaft assembly (230) and end effector (240) relative to handle assembly (220) about a longitudinal axis (261) defined by shaft assembly (230). By way of example only, rotation knob (231) and the associated components and features may be configured and operable in accordance with at least some of the teachings of U.S. Pat. No. 10,206,705, entitled "Features for Communication of Fluid through Shaft Assembly of Ultrasonic Surgical Instrument," issued Feb. 19, 2019, the disclosure of which is incorporated by reference herein.

Rotation knob (231) of shaft assembly (230) comprises a rotatable housing (236) that is rotatably disposed about outer tube (232). In one example, rotation knob (231) defines a hollow interior which may be filled with fluid coolant (263) and thereby can function as a fluid reservoir (262) for fluid coolant (263). Fluid reservoir (262) is configured to be filled with fluid coolant and to selectively retain the fluid coolant therein. Rotation knob (231) is fluidly coupled with outer tube (232) via an opening (264) defining a fluid passageway between fluid reservoir (262) and the fluid flow path toward ultrasonic blade (260), such as the space between inner tube (234) and outer tube (232) and/or a tube similar to tube (216) (see FIG. 5A). It should therefore be understood that tube (216) (see FIG. 5A) may be shortened or even omitted, such that tube (216) (see FIG. 5A) need not extend along the entire length of shaft assembly (230).

To discharge fluid coolant (263) from fluid reservoir (262) and along shaft assembly (230), rotation knob (231) further includes a pump, such as a plunger (270). Plunger (270) includes an arm (272) coupled to a fluid actuator (274) selectively operable by operator. In at least one example, as shown in FIGS. 6A-6C, fluid actuator (274) is a slidable push-tab located on handle assembly (220). Fluid actuator (274) is operatively coupled to plunger (270) and permits operator to slide push-tab (274) distally toward shaft assembly (230) to move plunger (270) distally away from body (222) within rotation knob (231) thereby discharging fluid coolant (263) out of rotation knob (231) via opening (264) and distally within shaft assembly (230). Opening (264) in one example includes a flexible seal member (not shown) operable as a one-way valve (not shown) to permit fluid coolant (263) to pass through opening (264) once adequate pressure builds within in fluid reservoir (262) as plunger (270) moves distally through fluid reservoir (262). Flexible seal member (not shown) is conversely operable to seal opening (264) if fluid coolant (263) is not discharging into shaft assembly (230) and inhibits fluid coolant (263) from flowing back into fluid reservoir (262) from shaft assembly (230).

As shown in FIG. 6A, to fill fluid reservoir (262) with fluid coolant (263), rotation knob (231) includes an access port (266) which permits operator to insert fluid coolant (263) into fluid reservoir (262). One method of inserting fluid coolant (263) is by use of a syringe (268). In one example, fluid reservoir (262) may comprise a septum (not shown) on its exterior which provides access through access port (266) and provides fluid access to an interior of fluid reservoir (262). A syringe (268) filled with fluid coolant (263) pierces through septum (not shown) such that fluid coolant (263) may be inserted into fluid reservoir (262) by discharging fluid coolant (263) from syringe (268). Alternatively, any other suitable access port and/or fluid coolant insertion mechanism may be utilized to fill fluid reservoir (262) with fluid coolant (263).

As described above, plunger (270) is operable to force fluid coolant (263) out of fluid reservoir (262) via opening (264) and toward end effector (240) (see FIG. 5A). In a fluid discharging motion, plunger (270) is moved distally within fluid reservoir (262) to apply pressure and thereby discharge fluid coolant (263). In a plunger return motion, such as for re-refilling fluid reservoir (262), a replacement medium such as air will replace the discharged fluid coolant (263) within fluid reservoir (262). To permit air to flow into fluid reservoir (262) as plunger (270) is moved proximally away from end effector (240) (see FIG. 5A), access port (266) acts as a vent to allow air to pass through and into fluid reservoir (262) as a vacuum is created by the movement of plunger (270). In some alternative examples, access port (266) can be located at or near distal end (276) of rotation knob (231), thereby permitting air to refill from distal end (276) of fluid reservoir (262) as plunger (270) moves in the proximal direction.

FIG. 6B depicts fluid reservoir (262) of instrument (200) filled with fluid coolant (263). As discussed above, rotation knob (231) is capable of rotating about longitudinal axis (261) thereby rotating shaft assembly (230) and end effector (240) (see FIG. 5A) concurrently. This rotation capability remains operable before fluid reservoir (262) is filled with fluid coolant (263), while it is filled with fluid coolant (263), and/or during discharge of fluid coolant (263) therefrom. It should be understood that rotation knob (231) may be increased in size to thereby increase the size and fluid capacity of fluid reservoir (262).

FIG. 6C depicts plunger (270) being moved distally within fluid reservoir (262) of instrument (200) to discharge fluid coolant (263) toward ultrasonic blade (260) (see FIG. 5A). Specifically, pressurized fluid coolant (263) is driven through opening (264) to thereby provide fluid coolant (263) to ultrasonic blade (260) before, during, or after ultrasonic blade (260) (see FIG. 5A) is operated to clamp tissue in conjunction with clamp arm (244). Operator may selectively move plunger (270) thereby discharging fluid coolant (263) at any time by actuating fluid actuator (274). In the example shown, the operator may move slidable tab (274) distally to affect the discharge. Operation of fluid actuator (274) and blade cooling may be performed concurrent to operation of clamp arm (244) via clamp actuator (228) or independently and without necessitating operation of clamp actuator (228). Because blade cooling may be accomplished at any time without requiring actuation of clamp actuator (228), greater flexibility is provided to the operator regarding blade cooling. For example, the operator may prefer to withhold blade cooling at a particular instance after urging clamp actuator (228), the operator may prefer blade cooling at irregular intervals, or the operator may prefer to do so in lesser or greater amounts depending on the unique circumstances of any particular procedure.

As described in an example above, fluid coolant (263) is discharged out of fluid reservoir (262) via opening (264) and is configured to travel distally within cavity (219) (see FIG. 5A) of shaft assembly (230). In this example, the operator may opt to "prime" blade cooling system (241) by moving plunger (270) distally to a predisposed placement to discharge fluid coolant (263) into cavity (219) and therefore prepare instrument (200) for quicker blade cooling during use. As such, cavity (219) (see FIG. 5A) may include a one-way seal positioned at or near the distal end of shaft assembly (230) which is operative to inhibit fluid coolant (263) from unintentionally leaking from cavity (219) (see FIG. 5A) while instrument (200) is in use and is operative to selectively allow fluid coolant (263) to exit cavity (219) (see FIG. 5A) toward ultrasonic blade (260) (see FIG. 5A).

FIGS. 7A-7B shows a one-way valve, such as an exemplary wiper seal (221), positioned within cavity (219) to selectively permit fluid coolant (263) to discharge toward ultrasonic blade (260) (see FIG. 5A). Outer edge (223) of wiper seal (221) fixedly attaches to inner surface (225) of outer tube (232) while inner edge (227) of wiper seal (221) creates a detachable fluid seal with outer surface (235) of inner tube (234) thereby selectively blocking or permitting cooling fluid (263) to pass wiper seal (221) as fluid pressure is applied by plunger (270) (see FIG. 6A). FIG. 7A shows wiper seal (221) in a first configuration sealing fluid coolant (263) within cavity (219). FIG. 7B shows wiper seal (221) in a second configuration allowing fluid coolant (263) to pass by wiper seal (221). In the first configuration of FIG. 7A, inner edge (227) of wiper seal (221) extends proximally within cavity (219) of shaft assembly (230) and contacts inner tube (234) to create the fluid seal. In the second configuration, inner edge (227) of wiper seal (221) inverts due to the fluid pressure and extends distally within cavity (219) of shaft assembly (230). While in the second configuration, wiper seal (221) may be induced to create a gap (233) for fluid coolant (263) to pass through for cooling.

In a first example, to affect the transition of wiper seal (221) from the first configuration to the second configuration, distal movement of plunger (270) within fluid reservoir (262) pressurizes fluid coolant (263) within cavity (219) to overcome the strength of the fluid seal and force wiper seal (221) into the second configuration and to release fluid coolant (263). In a second example, wiper seal (221) remains biased in the first configuration (shown in FIG. 7A) due to pressure induced within cavity (219) while clamp arm (244) is in a closed (clamped) position, and wiper seal (221) transitions to the second configuration (shown in FIG. 7B) upon releasing of clamp actuator (228) to return clamp arm (244) back to its home position. Thereafter, selective activation of fluid actuator (274) by the operator releases fluid coolant (263) through gap (233) created in the fluid seal. In this second example, fluid coolant (263) is inhibited from being discharged toward ultrasonic blade (260) (see FIG. 5A) while a tissue clamping operation is being performed, but permitted while clamp arm (244) (see FIG. 5A) is released to its home (unclamped) position.

B. Exemplary Ultrasonic Surgical Instrument with Automated Cooling Delivery

FIG. 8 illustrates a fourth exemplary ultrasonic surgical instrument (300) with a blade cooling system (341) that is configured to operate substantially similar to instruments (100, 200) discussed above except for the differences discussed below. It should therefore be understood that instrument (300) may include the same components and operabilities as instruments (100, 200), in addition to including the components and operabilities described below. Instrument (300) of the present example comprises a body (322), a shaft assembly (330), and end effector (240) (see FIG. 5A). As with instruments (100, 200) discussed above, body (322) is configured to receive an ultrasonic transducer assembly (not shown). Body (322) also includes a handle assembly (320) having a pistol grip (324) and a pair of buttons (326). Handle assembly (320) includes a clamp actuator (328) that is pivotable toward and away from pistol grip (324). Similar to instruments (100, 200), instrument (300) includes end effector (240) (see FIG. 5A) having ultrasonic blade (260) (see FIG. 5A) and pivoting clamp arm (244) (see FIG. 5A). Clamp arm (244) (see FIG. 5A) is coupled with clamp actuator (328) such that clamp arm (244) (see FIG. 5A) is pivotable toward ultrasonic blade (260) (see FIG. 5A) in response to pivoting of clamp actuator (328) toward pistol grip (324); and such that clamp arm (244) (see FIG. 5A) is pivotable away from ultrasonic blade (260) (see FIG. 5A) in response to pivoting of clamp actuator (328) away from pistol grip (324).

Shaft assembly (330) of the present example comprises an outer sheath, or outer tube (332), and inner tube (234) (see FIG. 5A). Inner tube (234) (see FIG. 5A) of this example is slidably disposed within outer tube (332) such that inner tube (234) (see FIG. 5A) translates longitudinally within outer tube (332) relative to outer tube (332) to selectively pivot clamp arm (244) (see FIG. 5A) toward and away from ultrasonic blade (260) (see FIG. 5A). In addition, at least one of body (322) or shaft assembly (330) includes a rotation knob (331) configured to provide fluid communication similar to rotation knob (231) (see FIG. 6A) described above; however, rotation knob (331) is not equipped with fluid reservoir (262) (see FIG. 6A) in the present example. Rather, at least one of body (322) or shaft assembly (330) includes various components of blade cooling system (341) which addresses similar issues as instrument (200) with regard to satisfying the desire to selectively cool ultrasonic blade (260) (see FIG. 5A).

Blade cooling system (341) of this example includes a pump, such as a syringe (340), which is filled with a fluid coolant (363) and selectively delivered to shaft assembly (330) by a tube (342) routed through rotation knob (331). Similar to instrument (200), shaft assembly (330) includes cavity (219) (see FIG. 7A), which is between outer tube (332) and inner tube (234) (see FIG. 7A) and operable to transmit fluid coolant (363) to ultrasonic blade (260) (see FIG. 5A). Alternatively, tubing may be positioned through shaft assembly (330) between outer tube (332) and inner tube (234) (see FIG. 7A) to directly deliver fluid coolant (363) from blade cooling system (341) to ultrasonic blade (260) (see FIG. 5A). Blade cooling system (341) further includes an actuator (344), such as a linear solenoid actuator, which is electrically connected to a device circuit (not shown) by electrical wiring (346). The device circuit (not shown) may be, for example, similar in structure and/or function to circuit board (34) (see FIG. 1) of instrument (10) (see FIG. 1). Actuator (344) is configured to receive commands from the device circuit (not shown) to automatically control release of fluid coolant (363) through tube (342) and toward ultrasonic blade (260) (see FIG. 5A), as needed as determined by the control system. It should be understood that similar devices and mechanisms, such as alternative pumps, could be utilized in place of syringe (340) for discharging fluid coolant (363).

Exemplary blade cooling system (341) of instrument (300) automates blade cooling so the operator does not have to selectively actuate the blade cooling during operation of instrument (300). Although operators may be able to discern when ultrasonic blade (260) (see FIG. 5A) requires cooling, it may be difficult in some instances for the operator to know exactly how hot ultrasonic blade (260) (see FIG. 5A) is after heated beyond certain temperatures. This may be especially difficult considering blade temperature may increase exponentially as it comes into contact with clamp arm (244) (see FIG. 5A). By providing automated blade cooling delivery, instrument (300) may thus inhibit potential blade heat-related issues which may arise when operators have control over blade cooling system (341). In one example, automated blade cooling may inhibit the operator from unnecessarily over-cooling ultrasonic blade (260) (see FIG. 5A) which can result in slower transections, etc. In an alternative example, under-cooling the ultrasonic blade can result in burn-through of padding on clamp arm (244) (see FIG. 5A) or damage to surrounding tissue.

Automated ultrasonic blade cooling is operable based on a measurement of blade frequency, wherein the control variable is a fluid coolant (363) drip rate or any other measurable method of cooling fluid delivery. As such, as shown in FIG. 8, syringe (340) can be stored in body (322) and actuated based on sensed increases in temperature of ultrasonic blade (260) (see FIG. 5A). In one example, actuator (344) is also positioned in body (322) and coupled to syringe (340) and device circuit (not shown) and selectively controlled by a proportional-integral-derivative controller ("PID") to inhibit fluid coolant (363) delivery while clamp actuator (328) and clamp arm (244) (see FIG. 5A) are making contact, for example, using impedance spectroscopy. In another example, blade cooling system (341) allows fluid coolant (363) delivery to ultrasonic blade (260) (see FIG. 5A) while clamp arm (244) (see FIG. 5A) is an in open (non-actuated) position and disallows fluid coolant (363) delivery while clamp arm (see FIG. 5A) is in the closed (actuated) position. In still another example, blade cooling system (341) initiates fluid coolant (363) discharge to ultrasonic blade (260) (see FIG. 5A) when desired due to particular blade-temperature conditions, as will be described below.

Figure 9:
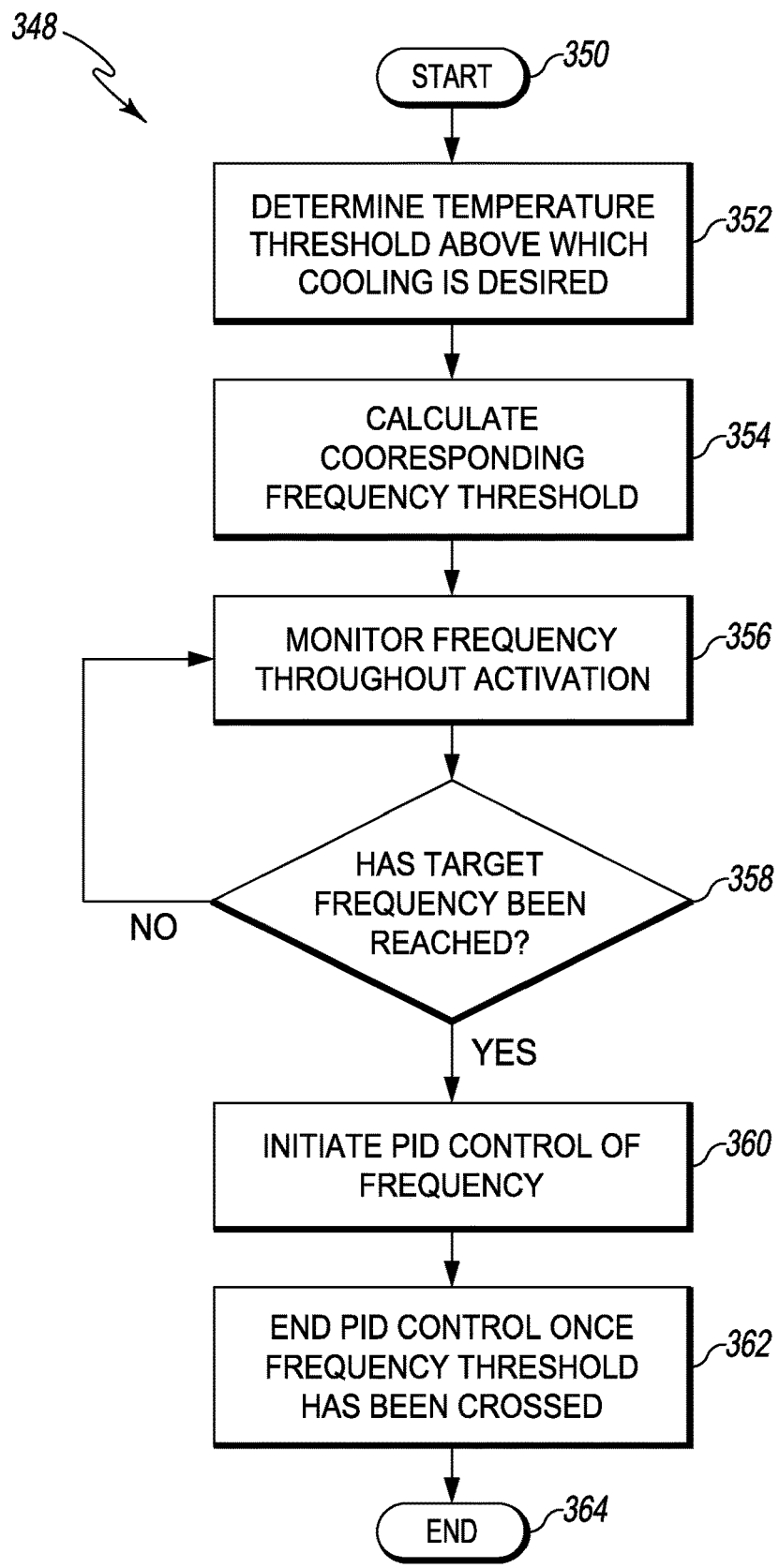
FIG. 9 depicts a flowchart representing an exemplary method for cooling an ultrasonic blade of the ultrasonic surgical instrument of FIG. 8.

FIG. 9 shows a flowchart representing an exemplary method (348) and/or control logic for cooling ultrasonic blade (260) (see FIG. 5A) of instrument (300) (see FIG. 8). Such control logic of the present example is performed on a control module (not shown) having a microprocessor (not shown) and a memory (not shown). At step (350), the control module (not shown) begins the exemplary routine which develops the frequency-temperature behavior for a given blade-transducer pair, wherein temperature is a function of the frequency: temp=F(frequency). At step (352), control module (not shown) determines the temperature threshold above which cooling is desired. At step (354), the control module (not shown) calculates the corresponding frequency threshold, referred to herein as the "target frequency." At step (356), control module (not shown) monitors the frequency throughout activation of ultrasonic blade (260) (see FIG. 5A). At step (358), control module (not shown) determines whether the target frequency has been reached. If the target frequency has not been reached, control module (not shown) returns to step (356). If the target frequency has been reached, control module (not shown) moves to step (360) and initiates PID control of the frequency using the fluid coolant (363) drip rate as a control variable in the function: $U(t)=K^*e(t)+K_I\int^{\tau}e(\tau)de+k_D(de(t)/dt)$, wherein e=(frequency−target frequency). Next, at step (362), control module (not shown) ends PID control once the frequency has been crossed, thus indicating ultrasonic blade (260) (see FIG. 5A) has been adequately cooled and the control system may end, at step (364), if the operation has ended or may otherwise continuously return to step (356) and repeat the methods described herein.

Figure 10:
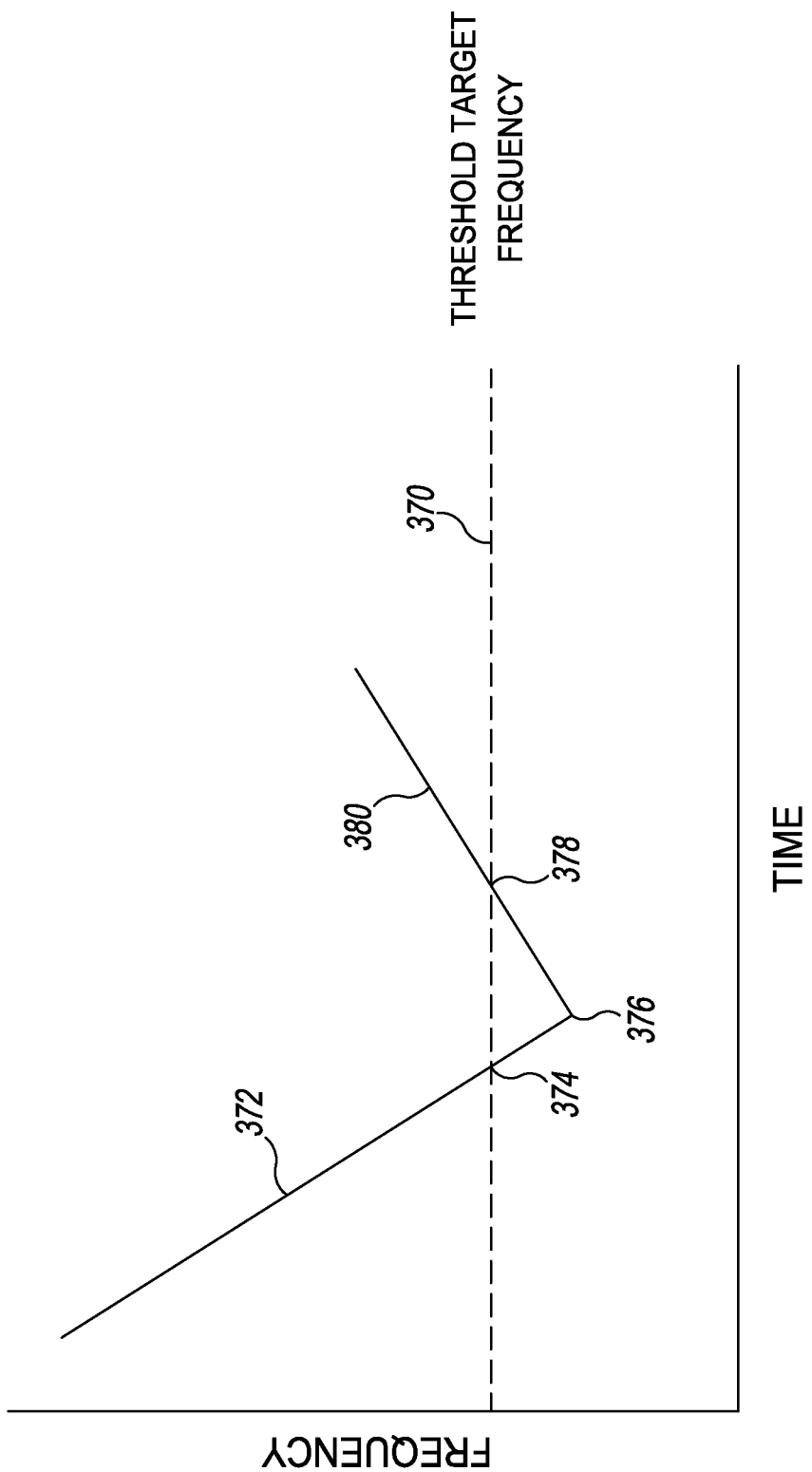
FIG. 10 depicts a line graph illustrating an example data set resulting from the exemplary method for cooling the ultrasonic blade of FIG. 9.

FIG. 10 shows an illustrative example of an exemplary control logic method (348) of FIG. 9. Once a target frequency (370) has been determined, the control module (not shown) will continuously monitor the frequency of ultrasonic blade (260) (see FIG. 5A) during operation to determine whether the target frequency has been reached, which is reflected by a decreasing frequency portion (372) wherein the frequency is continually decreased to approach target frequency (370). Once the target frequency is crossed, at frequency (374), the control module (not shown) determines that the target frequency has been crossed and thereby initiates PID control of the frequency at frequency (376), corresponding to step (360) of method (348). Once the frequency threshold has again been crossed at frequency (378), control module (not shown) ends PID control and ultrasonic blade frequency (380) may continue un-controlled until the control module (not shown) re-evaluates and initiates PID control.

C. Exemplary Ultrasonic Surgical Instrument with Diaphragm Pump

Figure 11A:
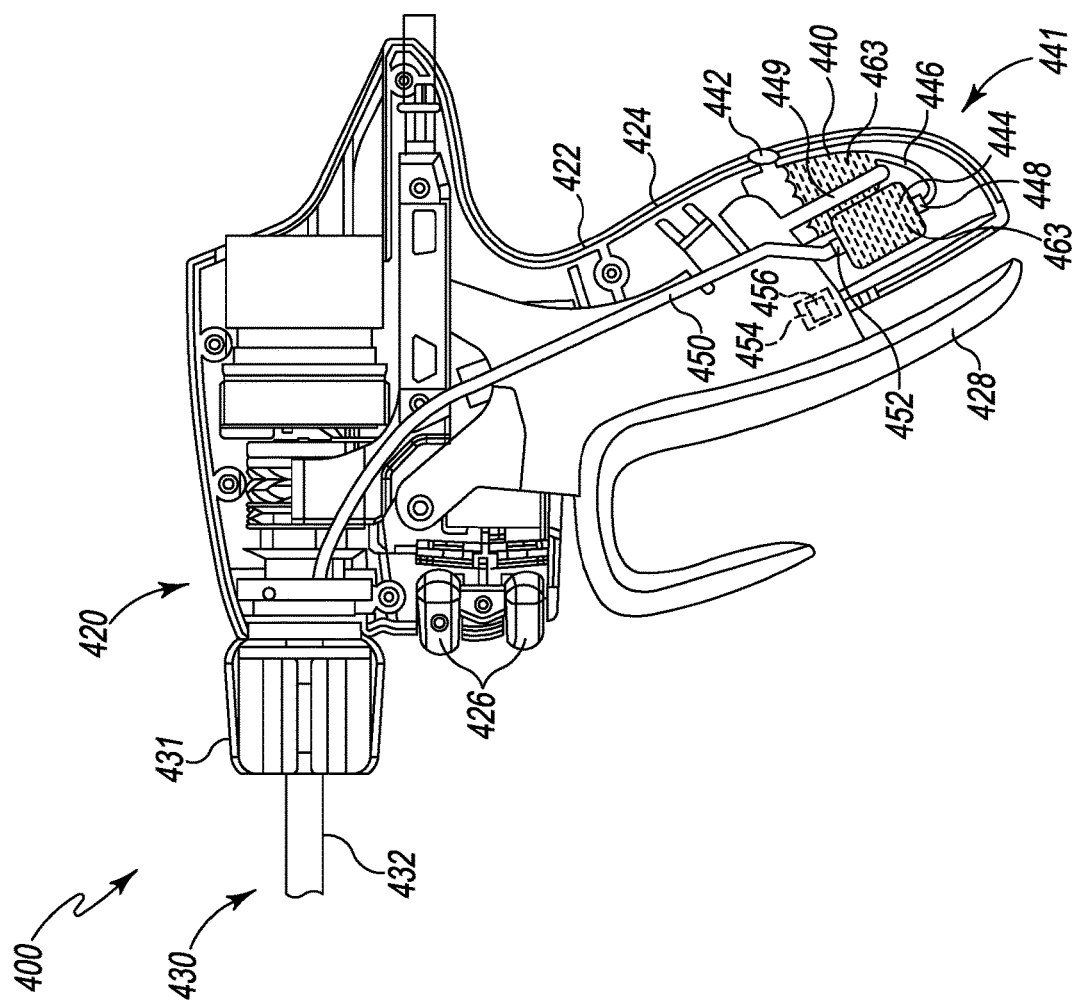
FIG. 11A depicts a side elevational view of a fifth exemplary ultrasonic surgical instrument with a housing shroud removed for greater clarity and a clamp actuator in a first position.
Figure 11B:
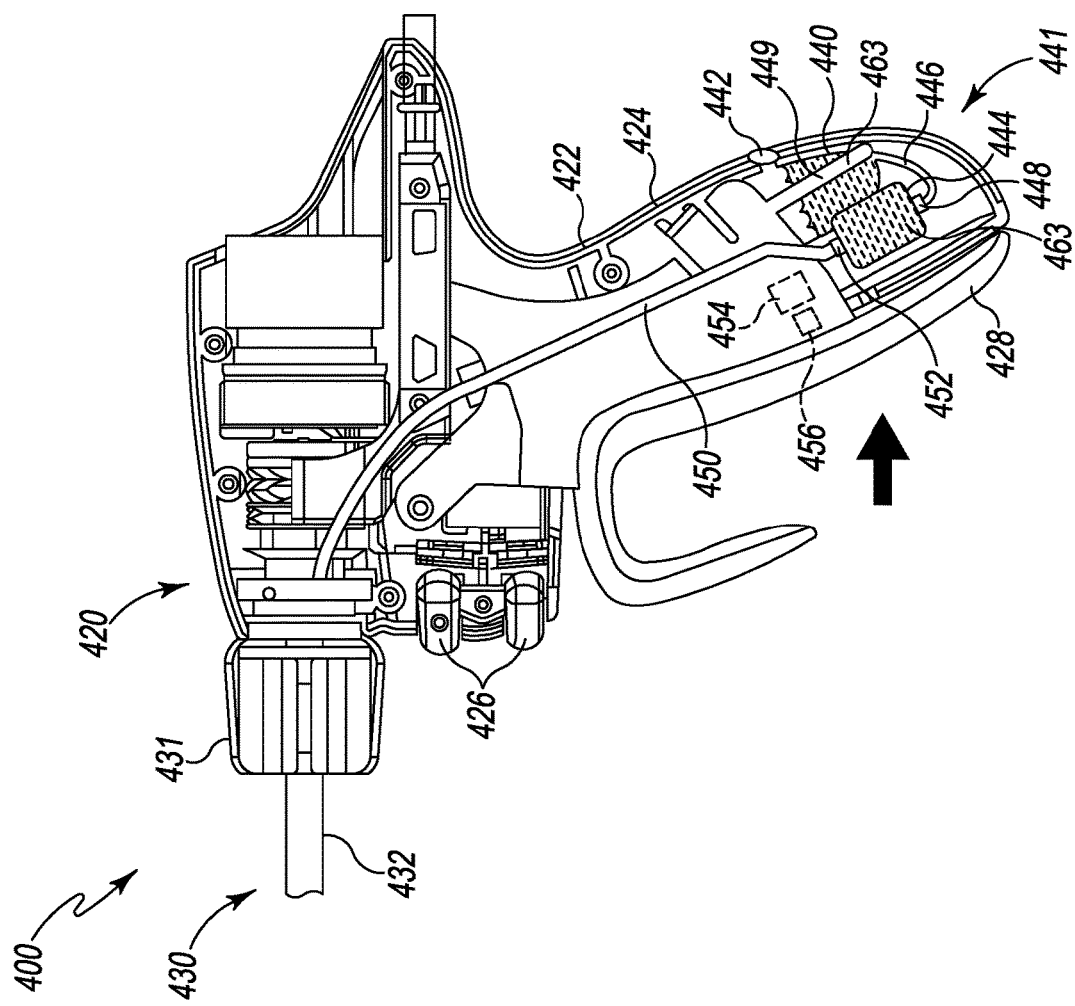
FIG. 11B depicts the side elevational view of the ultrasonic surgical instrument similar to FIG. 11A, but showing the clamp actuator in a second position.
Figure 11C:
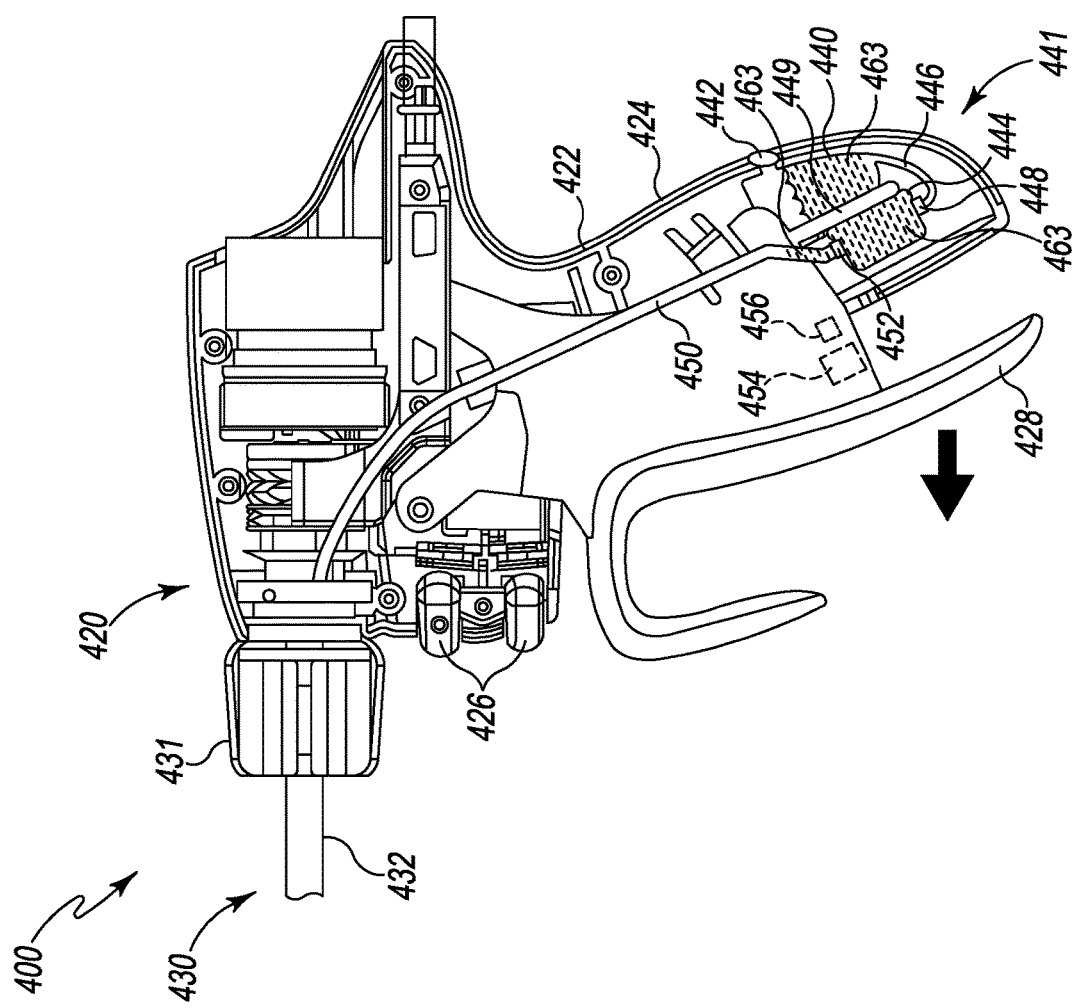
FIG. 11C depicts the side elevational of the ultrasonic surgical instrument similar to FIG. 11B, but showing the clamp actuator in a third position.

FIGS. 11A-11C illustrate a fifth exemplary ultrasonic surgical instrument (400) with a blade cooling system (441) configured to operate substantially similar to instruments (100, 200, 300) discussed above except for the differences discussed below. It should therefore be understood that instrument (400) may include the same components and operabilities as instrument (100, 200, 300), in addition to including the components and operabilities described below. Instrument (400) of the present example comprises a body (422), a shaft assembly (430), and end effector (240) (see FIG. 5A). As with instruments (100, 200, 300) discussed above, body (422) is configured to receive an ultrasonic transducer assembly (not shown). Body (422) also includes a handle assembly (420) having a pistol grip (424) and a pair of buttons (426). Handle assembly (420) includes a clamp actuator (428) that is pivotable toward and away from pistol grip (424). Similar to instruments (100, 200, 300), instrument (400) includes end effector (240) (see FIG. 5A) having ultrasonic blade (260) (see FIG. 5A) and pivoting clamp arm (244) (see FIG. 5A). Clamp arm (244) (see FIG. 5A) is coupled with clamp actuator (428) such that clamp arm (244) (see FIG. 5A) is pivotable toward ultrasonic blade (260) (see FIG. 5A) in response to pivoting of clamp actuator (428) toward pistol grip (424); and such that clamp arm (244) (see FIG. 5A) is pivotable away from ultrasonic blade (260) (see FIG. 5A) in response to pivoting of clamp actuator (428) away from pistol grip (424).

Shaft assembly (430) of the present example comprises an outer sheath, or outer tube (432), and inner tube (234) (see FIG. 5A). Inner tube (234) (see FIG. 5A) of this example is slidably disposed within outer tube (432) such that the inner tube (234) (see FIG. 5A) translates longitudinally within outer tube (432) relative to outer tube (432) to selectively pivot clamp arm (244) (see FIG. 5A) toward and away from ultrasonic blade (260) (see FIG. 5A). In addition, at least one of body (422) or shaft assembly (430) includes a rotation knob (431) configured to provide fluid communication similar to rotation knob (231) (see FIG. 6A) described above; however, rotation knob (431) is not equipped with fluid reservoir (262) (see FIG. 6A). Rather, at least one of body (422) or shaft assembly (430) includes multiple components of blade cooling system (441) which addresses similar issues as instrument (200) with regard to satisfying the desire to selectively cool the ultrasonic blade.

Blade cooling system (441) of instrument (400) includes a fluid reservoir (440) configured to store fluid coolant (463). Fluid reservoir (440) is positioned within body (422) and is accessible for inserting fluid coolant (463) by an access port (442). Alternatively, fluid reservoir (440) may be coupled with body (422) or otherwise positioned within handle assembly (420) in any suitable manner as would be apparent to one of ordinary skill in the art. One method of inserting fluid coolant (463) is by use of a syringe, such as syringe (268) (see FIG. 6A). In one example, fluid reservoir (440) has a septum (not shown) on its exterior which provides access through access port (442) and provides fluid access to the interior of fluid reservoir (440). Syringe (268) (see FIG. 6A) filled with fluid coolant (463) pierces through the septum (not shown) such that fluid coolant (463) is inserted into fluid reservoir (440) by discharging fluid coolant (463) from syringe (268) (see FIG. 6A). Alternatively, any other suitable access port and/or fluid coolant insertion mechanism may be utilized to fill fluid reservoir (440) with fluid coolant (463).

Blade cooling system (441) of instrument (400) further includes a pump having a flexible diaphragm, such as a fluid bladder (444), in fluid connection with fluid reservoir (440) via tube (446). Tube (446) permits fluid coolant (463) to fill fluid bladder (444) and remain in fluid bladder (444) until actuated by operator. To inhibit fluid coolant (463) from returning to fluid reservoir (440), tube (446) includes a one-way fluid valve (448). Once fluid coolant (463) is moved into fluid bladder (444), fluid coolant (463) remains in fluid bladder (444) until fluid bladder (444) is compressed by protruding arm (449) of clamp actuator (428) thereby forcing fluid coolant (463) through a second tube (450) toward ultrasonic blade (260) (see FIG. 5A). More particularly, fluid coolant (463) is selectively delivered to shaft assembly (430) by tube (450) which is routed through rotation knob (431) and fluidly connects to shaft assembly (430). Similar to instrument (200), shaft assembly (430) includes cavity (219) (see FIG. 7A), which is between outer tube (432) and inner tube (234) (see FIG. 7A) and operable to transmit fluid coolant (463) to ultrasonic blade (260) (see FIG. 5A). Alternatively, tubing can be positioned through shaft assembly (430) between outer tube (432) and inner tube (234) (see FIG. 7A) to directly deliver fluid coolant (463) from blade cooling system (441) to ultrasonic blade (260) (see FIG. 5A). Similar to one-way fluid valve (448) of tube (446), tube (450) also includes a one-way fluid valve (452) to inhibit fluid coolant (463) from returning to fluid bladder (444).

Instrument (400) provides operator with the ability to initiate ultrasonic blade cooling at any point during operation of instrument (400) by extending clamp actuator (428) distally away from body (422) such that a pin (454) overcomes a detent (456) to permit clamp actuator (428) to extend away from body (422). In one example, pin (454) is located on clamp actuator (428) while detent (456) is located on body (422). In an alternative example, pin (454) is located on body (422) while detent (456) is located on clamp actuator (428). This detent locking mechanism provides a guard against unwanted forward extension of clamp actuator (428) and therefore unwanted ultrasonic blade cooling.

By extending clamp actuator (428) distally away from body (422), protruding arm (449) compresses fluid bladder (444) and thereby pumps fluid coolant (463) toward ultrasonic blade (260) (see FIG. 5A). To initiate use of instrument (400), the operator may fill fluid reservoir (440) with fluid coolant (463) as described above, and then "prime" blade cooling system (441) by extending clamp actuator (428) distally away from body (422) to compress fluid bladder (444) until fluid coolant (463) exits near ultrasonic blade (260) (see FIG. 5A). At this point, instrument (400) is prepared for operation as tube (450) and shaft assembly (430) are filled with fluid coolant (463). During operation, any time the operator wishes to initiate ultrasonic blade cooling, the operator can extend clamp actuator (428) forward to discharge fluid coolant (463).

With respect to FIG. 11A, clamp actuator (428) of instrument (400) is in a resting/home position. In this configuration, clamp arm (244) (see FIG. 5A) of end effector (240) (see FIG. 5A) remains in an open (non-pivoted) state with regard to ultrasonic blade (240) (see FIG. 5A), and fluid bladder (444) remains in an uncompressed state thereby inhibiting fluid coolant (463) discharge through tube (450), toward shaft assembly (430), and, ultimately, ultrasonic blade (240) (see FIG. 5A) for cooling.

FIG. 11B shows instrument (400) with clamp actuator (428) in an actuated (clamped) position. In this configuration, clamp arm (244) (see FIG. 5A) of end effector (240) (see FIG. 5A) is pivoted closed toward ultrasonic blade (240) (see FIG. 5A) to clamp tissue, and fluid bladder (444) still remains in an uncompressed state thereby inhibiting fluid coolant (463) discharge through tube (450), toward shaft assembly (430), and, ultimately, to ultrasonic blade (240) (see FIG. 5A) for cooling.

FIG. 11C shows instrument (400) with clamp actuator (428) in a distally extended position. In this configuration, clamp arm (244) (see FIG. 5A) of end effector (240) (see FIG. 5A) remains in an open (non-pivoted) state with regard to ultrasonic blade (240) (see FIG. 5A), pin (454) has overcome and moved beyond detent (456), and fluid bladder (444) is in a compressed state. During such compression, fluid bladder (444) directs fluid coolant (463) through tube (450), toward shaft assembly (430), and, ultimately, to ultrasonic blade (240) (see FIG. 5A) for cooling. As such, ultrasonic blade cooling may be achieved at any time irrespective of operation of clamp arm (244) (see FIG. 5A).

Figure 12A:
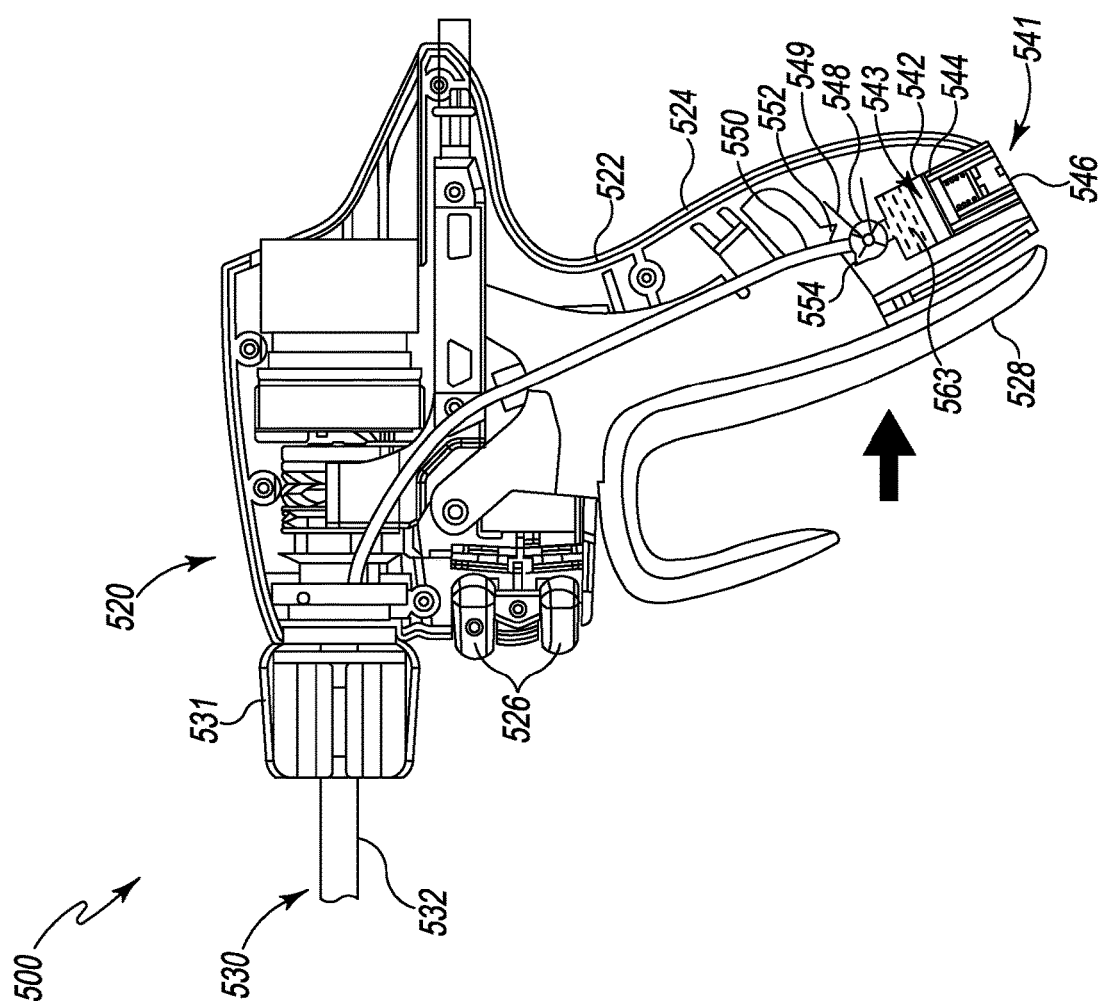
FIG. 12A depicts a side elevational view of a sixth exemplary ultrasonic surgical instrument with a housing shroud removed and a clamp actuator in a first position.
Figure 12B:
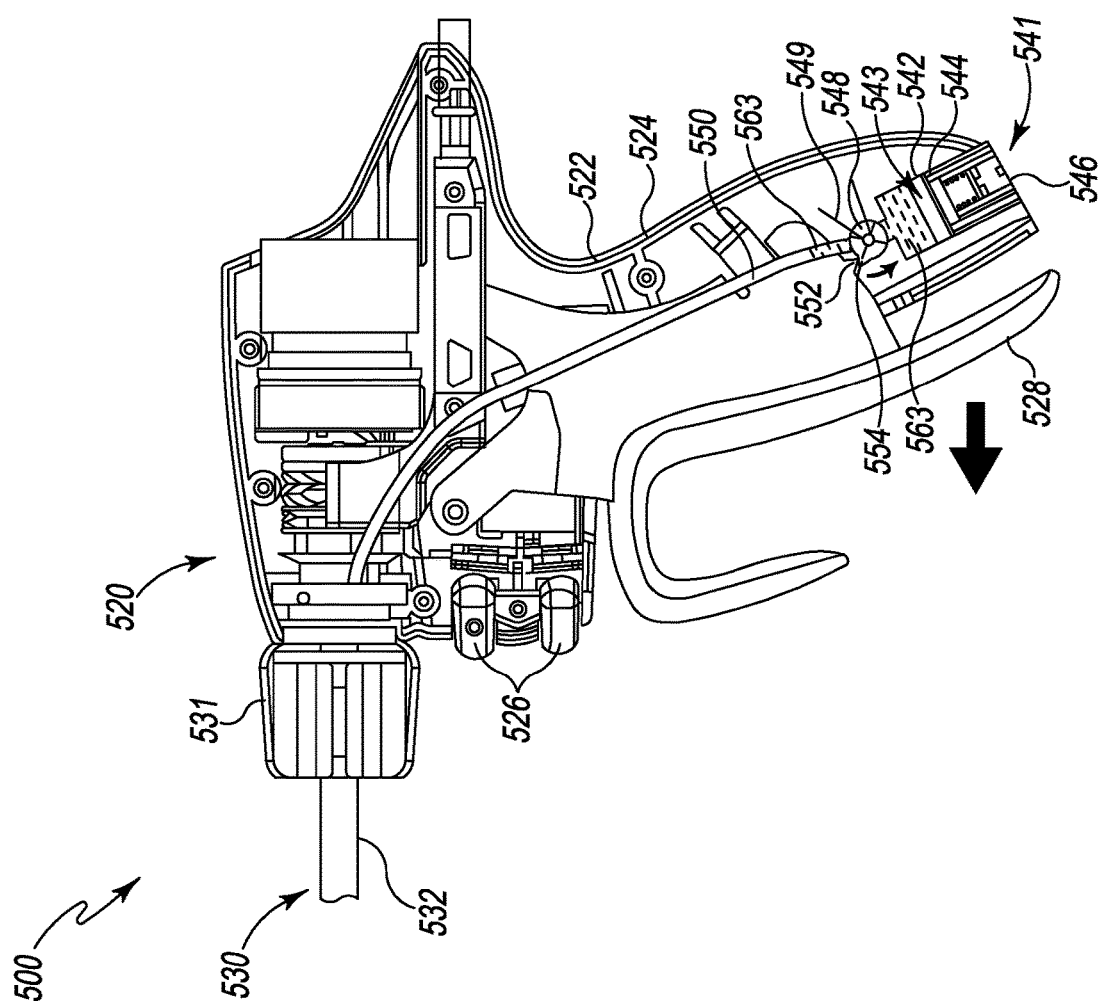
FIG. 12B depicts the side elevational view of the ultrasonic surgical instrument similar to FIG. 12A, but showing the clamp actuator in a second position.
Figure 13:
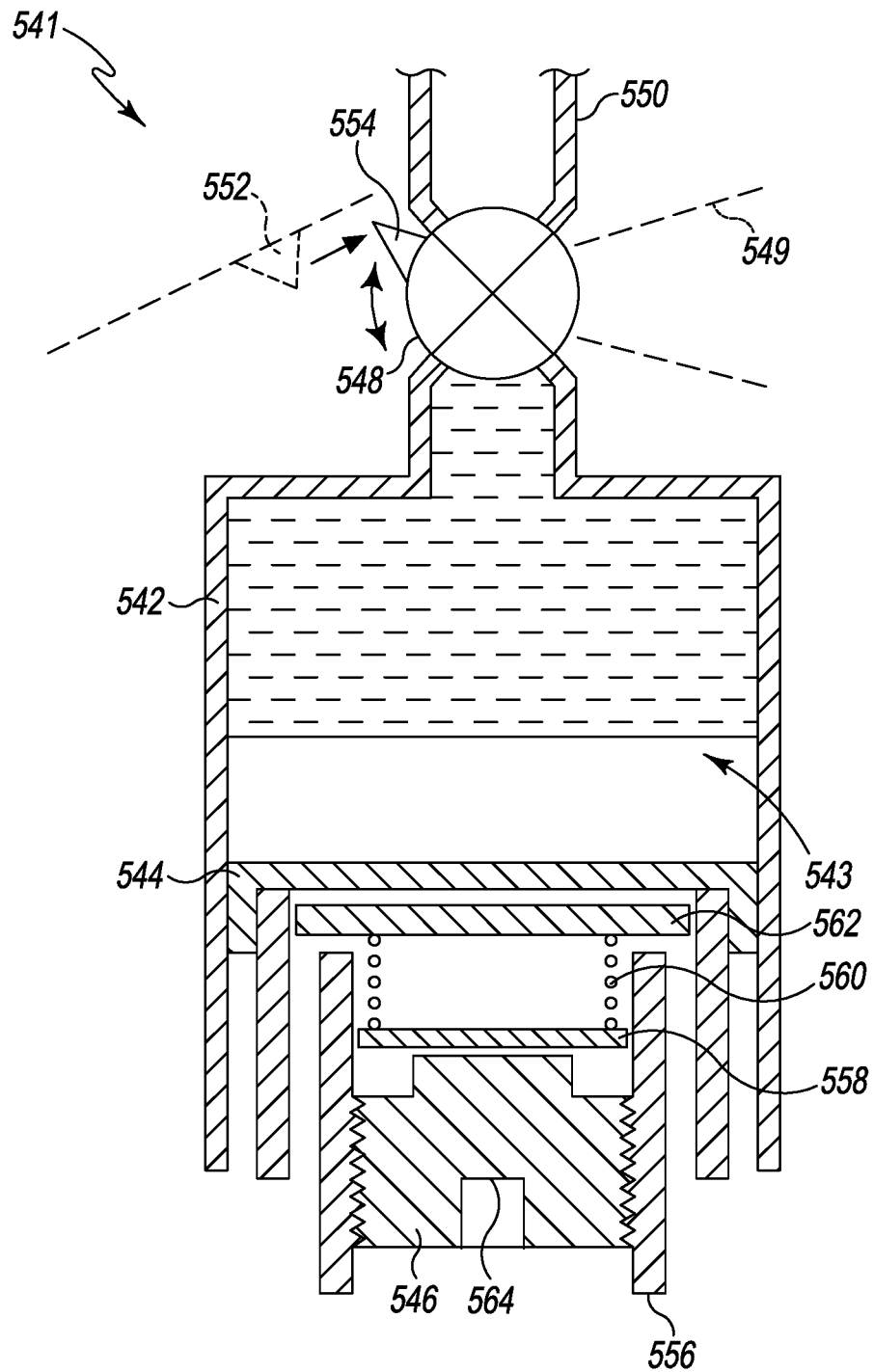
FIG. 13 depicts a sectional side view of a fluid reservoir of the ultrasonic surgical instrument of FIG. 12A.

D. Exemplary Ultrasonic Surgical Instrument with Spring Loaded Pressurized Syringe FIGS. 12A, 12B, and 13 illustrate a sixth exemplary ultrasonic surgical instrument (500) with a blade cooling system (541) configured to operate substantially similar to instruments (100, 200, 300, 400) discussed above except for the differences discussed below. It should therefore be understood that instrument (500) may include the same components and operabilities as instrument (100, 200, 300, 400), in addition to including the components and operabilities described below. Instrument (500) of the present example comprises a body (522), a shaft assembly (530), and end effector (240) (see FIG. 5A). As with instruments (100, 200, 300, 400) discussed above, body (522) is configured to receive an ultrasonic transducer assembly (not shown). Body (522) also includes a handle assembly (520) having a pistol grip (524) and a pair of buttons (526). Handle assembly (520) includes a clamp actuator (528) that is pivotable toward and away from pistol grip (524). Similar to instruments (100, 200, 300, 400), instrument (500) includes end effector (240) (see FIG. 5A) having ultrasonic blade (260) (see FIG. 5A) and a pivoting clamp arm (244) (see FIG. 5A). Clamp arm (244) (see FIG. 5A) is coupled with clamp actuator (528) such that clamp arm (244) (see FIG. 5A) is pivotable toward ultrasonic blade (260) (see FIG. 5A) in response to pivoting of clamp actuator (528) toward pistol grip (524); and such that clamp arm (244) (see FIG. 5A) is pivotable away from ultrasonic blade (260) (see FIG. 5A) in response to pivoting of clamp actuator (528) away from pistol grip (524).

Shaft assembly (530) of the present example comprises an outer sheath, or outer tube (532), and inner tube (234) (see FIG. 5A). Inner tube (234) (see FIG. 5A) of this example is slidably disposed within outer tube (532) such that inner tube (234) (see FIG. 5A) translates longitudinally within outer tube (532) relative to outer tube (532) to selectively pivot clamp arm (244) (see FIG. 5A) toward and away from ultrasonic blade (260) (see FIG. 5A). In addition, at least one of body (522) or shaft assembly (530) includes a rotation knob (531) operable to rotate shaft assembly (530) about its longitudinal axis, similar to instrument (200). Either one or both of body (522) or shaft assembly (530) includes various components of blade cooling system (541) which addresses similar issues as instrument (200) with regard to satisfying the desire to selectively cool ultrasonic blade (260) (see FIG. 5A).

Blade cooling system (541) of instrument (500) includes a syringe (542) housing fluid coolant (563), a pump, such as a plunger (544), a threaded plug (546), a valve (548), such as a spring-loaded valve, a delivery line (550), and a catch trigger (552) with a detent feature (554) to activate valve (548). In one example, valve (548) is spring-loaded via coupling to torsion spring (549), which is positioned within and coupled to body (522). Blade cooling system (541) is installed within body (522) such that syringe (542) is pre-filled with liquid coolant (563) and inserted into a position that syringe (542) fluidly couples with valve (548) and delivery line (550). Delivery line (550) is routed to shaft assembly (530) to permit ultrasonic blade cooling. For example, by routing through rotation knob (531), delivery line (550) discharges fluid coolant directly into cavity (219) (see FIG. 7A) between inner tube (234) (see FIG. 7A) and outer tube (532) for delivery to ultrasonic blade (260) (see FIG. 5A) similar to instrument (200). In an alternative example, delivery line (550) can routed though cavity (219) (see FIG. 7A) between inner tube (234) (see FIG. 7A) and outer tube (532) similar to instrument (200) discussed above.

Syringe (542) includes fluid coolant (563), air, or a combination of fluid coolant (563) and air in fluid reservoir (543). Fluid reservoir (543) of syringe (542) is configured to store, and be capable of discharging for blade cooling, approximately 120 drops (or about 6 milliliters) of fluid coolant (563), such as a liquid variant of fluid coolant (563), for each actuation cycle (rotation) of valve (548). In one example, between approximately 3 drops and approximately 5 drops, such as approximately 4 drops of fluid coolant (563), are discharged onto ultrasonic blade (260) (see FIG. 5A) per actuation, although it will be appreciated that any desired amount of fluid coolant (563) for cooling may be so used with any such instrument, such as those discussed herein. After use, syringe (542) may be sterilized, refilled with fluid coolant (563), and reused in later operations utilizing instrument (500).

Force is applied to syringe (542) to thereby discharge fluid coolant (563) into delivery line (550) upon rotation of valve (548). In the present example, plunger (544) of syringe (548) is configured to receive constant force to pressurize fluid reservoir (543) by threaded plug (546) being threaded into guide tube (556) to press against first bearing plate (558). First bearing plate (558) contacts compression spring (560), which maintains air compression against a second bearing plate (562), wherein second bearing plate (562) applies the constant pressure to plunger (544) for increasing fluid pressure within fluid reservoir (543). Guide tube (556) is fixedly grounded to body (522) to support movement and pressurization of other components of blade cooling system (541).

Threaded plug further includes a key (564), for example, an Allen wrench key, which permits operator to increase or decrease the force applied by compression spring (560) on plunger (560) within fluid reservoir (543). More particularly, threaded plug (546) is threaded into guide tube (556) during initial setup prior to operation of instrument (500) such that the initial spring (560) compression raises the fluid pressure within fluid reservoir (543) of syringe (542) to discharge fluid coolant (563) once valve (548) is actuated. During operation of instrument (500), catch trigger (552) and detent feature (554) interact each time clamp actuator (528) pivots toward body (522) to rotate valve (548) and, in turn, permit fluid coolant (563) to discharge into delivery line (550). In one example, catch trigger (552) is coupled to clamp actuator (528) and detent feature (554) is coupled to valve (548). In an alternative example, catch trigger (552) may be coupled to valve (548) and detent feature (554) may be coupled to clamp actuator (548).

As shown in FIG. 12A, clamp actuator (528) is squeezed such that catch trigger (552) and detent feature (554) are not in contact and valve (542) remains unrotated. Once clamp actuator (528) is released from being squeezed and returned to its home position, as shown in FIGS. 12B-13, catch trigger (552) momentarily contacts detent feature (554) to rotate valve (548). During this momentary rotation of valve (548), a fluid channel (not shown) defined within valve (548) fluidly connects to pressurized fluid reservoir (543) and fluid coolant (563) discharges into delivery line (550) until catch trigger (552) and detent feature (554) release and torsion spring (549) moves valve (548) back to its biased, fluidly closed, position.

Figure 14:
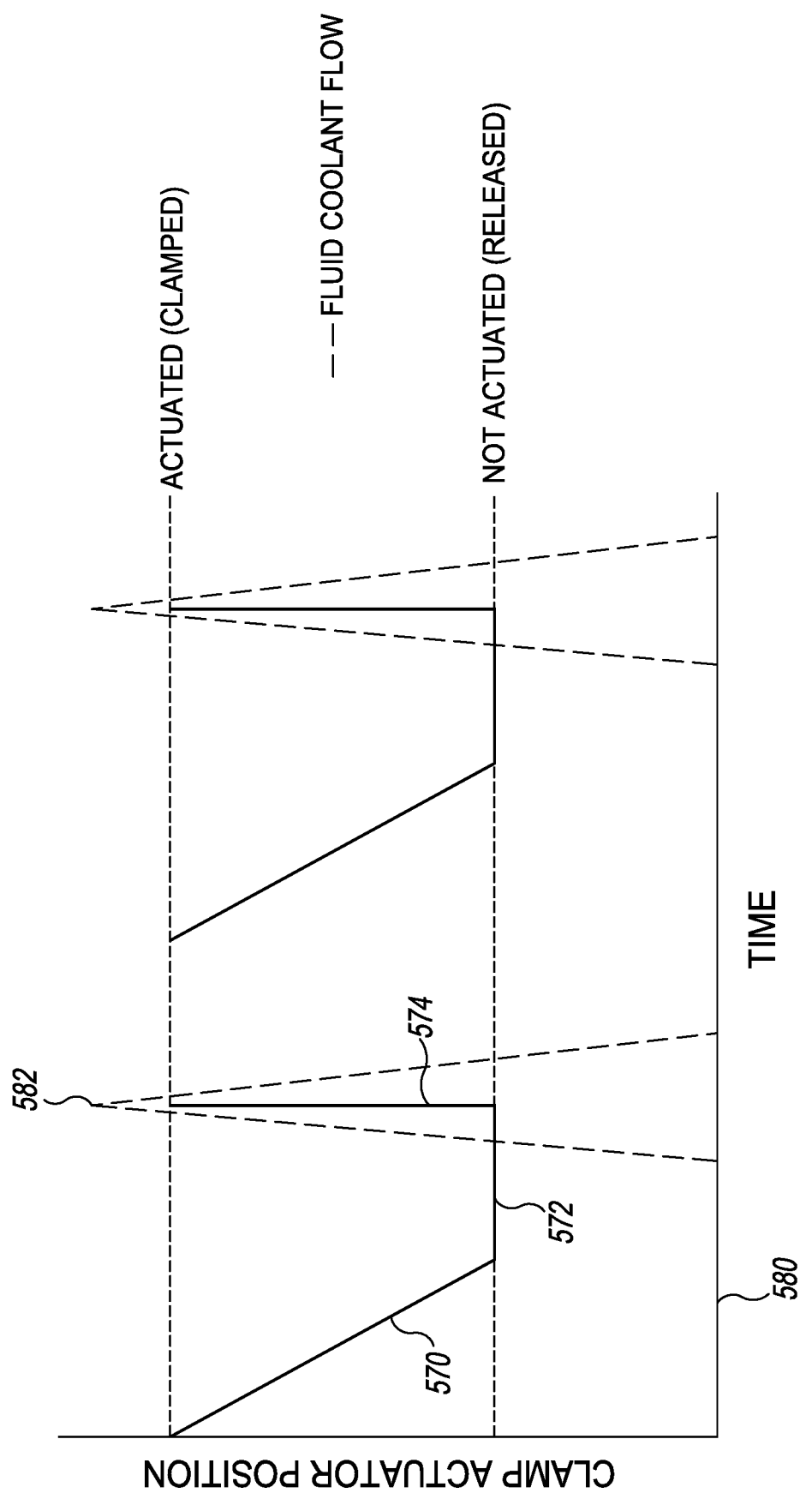
FIG. 14 depicts a line graph illustrating an example data set resulting from an exemplary method for cooling an ultrasonic blade of the ultrasonic surgical instrument of FIG. 12A.

FIG. 14 shows a graphical representation of fluid coolant (563) discharge flow as result of actuation of clamp actuator position (528). As described above and shown in FIG. 12A, fluid coolant (563) does not flow (580) during a first period (570) while clamp actuator (528) is in the process of being actuated/clamped to direct clamp arm (244) (see FIG. 5A) to clamp tissue. During a second period (572), clamp actuator (528) is fully actuated/clamped. As shown by FIG. 12B, during a third period (574), in which clamp actuator (528) is released to its biased/unclamped position, catch trigger (552) interacts with detent feature (554) to rotate valve (548) and discharge (582) fluid coolant (563) momentarily until catch trigger (552) and detent feature (554) release. This method of blade cooling repeats each time clamp actuator (528) is actuated during operation of instrument (500).

IV. EXEMPLARY COMBINATIONS

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

A surgical instrument, comprising: (a) a body; (b) a shaft assembly extending distally from the body and including an acoustic waveguide configured to couple with an ultrasonic transducer; (c) an end effector, including: (i) an ultrasonic blade in acoustic communication with the acoustic waveguide, and (ii) a clamp arm movably coupled relative to the ultrasonic blade and configured to move from an open position toward a closed position for compressing a tissue against the ultrasonic blade; (d) a clamp actuator movably coupled relative to the body and configured to selectively move from a first actuator position toward a second actuator position, wherein the clamp actuator is operatively coupled to the clamp arm to thereby direct movement of the clamp arm from the open position toward the closed position as the clamp actuator respectively moves from the first actuator position toward the second actuator position; (e) a blade cooling system operatively coupled to the clamp actuator and selectively operable to discharge a fluid coolant onto the ultrasonic blade while the clamp actuator remains in the first actuator position.

Example 2

The surgical instrument of Example 1, wherein the shaft assembly defines a longitudinal axis and further includes a knob operatively connected to the end effector, wherein the knob is configured to rotate about the longitudinal axis to thereby rotate the end effector about the longitudinal axis, and wherein the blade cooling system includes a fluid reservoir within the knob and configured to contain the fluid coolant therein.

Example 3

The surgical instrument of Example 2, wherein the blade cooling system further includes an access port positioned on the knob and in fluid communication with the fluid reservoir for introducing the fluid coolant into the fluid reservoir.

Example 4

The surgical instrument of any one or more of Examples 2 through 3, wherein the blade cooling system further includes a plunger positioned within the fluid reservoir and configured to selectively move therein for discharging the fluid coolant from the fluid reservoir.

Example 5

The surgical instrument of any one or more of Examples 2 through 4, wherein the blade cooling system further includes a fluid actuator operatively coupled to the plunger and configured to move the plunger for discharging the fluid coolant from the fluid reservoir.

Example 6

The surgical instrument of Example 5, wherein the fluid actuator is located on the body.

Example 7

The surgical instrument of any one or more of Examples 5 through 6, wherein the fluid actuator is a slidable push-tab operatively coupled to the plunger.

Example 8

The surgical instrument of any one or more of Examples 2 through 7, the shaft assembly further including: (i) an inner tube, (ii) an outer tube, and (iii) an interior space between the inner tube and the outer tube, wherein the interior space is in fluid communication with the fluid reservoir and configured to receive the fluid coolant discharged from the fluid reservoir for communication toward the ultrasonic blade.

Example 9

The surgical instrument of Example 8, wherein the blade cooling system further includes a fluid passageway fluidly connecting the fluid reservoir to the interior space of the shaft assembly, and wherein the plunger is operable to compress fluid coolant within the fluid reservoir thereby directing the fluid coolant through the fluid passageway.

Example 10

The surgical instrument of Example 9, wherein the blade cooling system further includes a one-way valve positioned within the fluid passageway, wherein the one-way valve is configured to allow the fluid coolant to flow from the fluid reservoir to the interior space, and wherein the one-way valve is configured to inhibit the fluid coolant from flowing from the interior space toward the fluid reservoir.

Example 11

The surgical instrument of any one or more of Examples 8 through 11, wherein the blade cooling system further includes a one-way fluid valve positioned in the interior space between the inner tube and the outer tube, wherein the one-way fluid valve is configured to allow the fluid coolant to distally flow through the interior space toward the end effector, and wherein the one-way valve is configured to inhibit the fluid coolant from proximally flowing through the interior space away from end effector.

Example 12

The surgical instrument of Example 1, the blade cooling system further including: (i) a fluid reservoir supported by the body and configured to contain the fluid coolant, and (ii) a fluid bladder positioned within the body, wherein the compressible fluid bladder is operable to receive the fluid coolant from the fluid reservoir via a first fluid passageway; and wherein the fluid bladder is operable to provide fluid coolant to the ultrasonic blade via a second fluid passageway.

Example 13

The surgical instrument of Example 12, wherein the clamp actuator is further configured to selectively move toward a third actuator position, wherein the clamp actuator is configured to compress the fluid bladder as the clamp actuator is moved toward the third actuator position for discharging the fluid coolant from the fluid bladder.

Example 14

The surgical instrument of any one or more of Examples 12 through 13, wherein the fluid bladder remains uncompressed in each of the first and the second actuator positions.

Example 15

The surgical instrument of any one or more of Examples 12 through 14, wherein at least one of the first and the second fluid passageways includes a one-way fluid valve.

Example 16

A surgical instrument, comprising: (a) a shaft assembly, including: (i) an acoustic waveguide configured to couple with an ultrasonic transducer, and (ii) a rotation knob operatively coupled to the shaft assembly, wherein the shaft assembly defines a longitudinal axis and the rotation knob is configured to rotate the shaft assembly about the longitudinal axis; (b) an end effector, including: (i) an ultrasonic blade in acoustic communication with the acoustic waveguide, and (ii) a clamp arm movably coupled relative to the ultrasonic blade and configured to move from an open position toward a closed position for compressing a tissue against the ultrasonic blade; (c) a clamp actuator configured to selectively move from a first actuator position toward a second actuator position, wherein the clamp actuator is operatively coupled to the clamp arm to thereby direct movement of the clamp arm from the open position toward the closed position as the clamp actuator respectively moves from the first actuator position toward the second actuator position; (d) a blade cooling system operably coupled to the clamp actuator and selectively operable to discharge fluid coolant onto the ultrasonic blade while the clamp actuator is in the first actuator position, comprising: (i) a fluid reservoir defined by a cavity within the rotation knob, and (ii) a plunger positioned within the fluid reservoir.

Example 17

The surgical instrument of Example 16, further comprising a fluid actuator operatively coupled to the plunger and configured to move the plunger for discharging the fluid coolant from the fluid reservoir.

Example 18

The surgical instrument of any one or more of Examples 16 through 17, the shaft assembly further comprising: (i) an inner tube, (ii) an outer tube, and (iii) an interior space between the inner tube and the outer tube, wherein the interior space is in fluid communication with the fluid reservoir and configured to receive the fluid coolant discharged from the fluid reservoir for communication toward the ultrasonic blade.

Example 19

A surgical instrument, comprising: (a) a shaft assembly including an acoustic waveguide configured to couple with an ultrasonic transducer; (b) an end effector, including: (i) an ultrasonic blade in acoustic communication with the acoustic waveguide, and (ii) a clamp arm movably coupled relative to the ultrasonic blade and configured to move from an open position toward a closed position for compressing a tissue against the ultrasonic blade; (c) a clamp actuator configured to selectively move from a first actuator position toward a second actuator position, wherein the clamp actuator is operatively coupled to the clamp arm to thereby direct movement of the clamp arm from the open position toward the closed position as the clamp actuator respectively moves from the first actuator position toward the second actuator position; (d) a blade cooling system operatively coupled to the clamp actuator and selectively operable to discharge a fluid coolant onto the ultrasonic blade while the clamp actuator remains in the first actuator position, comprising: (i) a fluid reservoir configured to store fluid coolant; and (ii) a compressible fluid bladder configured to receive fluid coolant from the fluid reservoir via a first fluid passageway, and wherein the fluid bladder is selectively operable to discharge the fluid coolant onto the ultrasonic blade via a second fluid passageway.

Example 20

The surgical instrument of Example 19, wherein the clamp actuator is further configured to selectively move toward a third actuator position, wherein the clamp actuator is configured to compress the fluid bladder as the clamp actuator is moved toward the third actuator position for discharging the fluid coolant from the fluid bladder.

V. MISCELLANEOUS

In some exemplary versions, the same vibrational movement that is used to drive an ultrasonic blade (24, 160) during tissue cutting/sealing may drive fluid coolant distally along blade (24, 160). As yet another merely illustrative example, fluid may be communicated to and/or along blade (24, 160) in accordance with at least some of the teachings of U.S. Pat. No. 8,591,459, entitled "Use of Biomarkers and Therapeutic Agents with Surgical Devices," issued Nov. 26, 2013, the disclosure of which is incorporated by reference herein. It should be understood that the teachings in U.S. Pat. No. 8,591,459 relating to dispensation of medical fluids may be readily adapted to provide communication of cooling fluid. It should also be understood that the teachings herein may be readily combined with the teachings of U.S. Pat. No. 10,206,705, entitled "Features for Communication of Fluid through Shaft Assembly of Ultrasonic Surgical Instrument," issued Feb. 19, 2019, the disclosure of which is incorporated by reference herein; U.S. Pub. No. 2016/0143659, entitled "Ultrasonic Surgical Instrument with Blade Cooling through Retraction," published May 26, 2016, issued as U.S. Pat. No. 10,433,863 on Oct. 8, 2019, the disclosure of which is incorporated by reference herein; and U.S. Pat. No. 10,034,685, entitled "Features to Apply Fluid to an Ultrasonic Blade of a Surgical Instrument," issued Jul. 31, 2018, the disclosure of which is incorporated by reference herein.

It should be understood that any of the versions of instruments described herein may include various other features in addition to or in lieu of those described above. By way of example only, any of the instruments described herein may also include one or more of the various features disclosed in any of the various references that are incorporated by reference herein. It should also be understood that the teachings herein may be readily applied to any of the instruments described in any of the other references cited herein, such that the teachings herein may be readily combined with the teachings of any of the references cited herein in numerous ways. Other types of instruments into which the teachings herein may be incorporated will be apparent to those of ordinary skill in the art.

It should also be understood that any ranges of values referred to herein should be read to include the upper and lower boundaries of such ranges. For instance, a range expressed as ranging "between approximately 1.0 inches and approximately 1.5 inches" should be read to include approximately 1.0 inches and approximately 1.5 inches, in addition to including the values between those upper and lower boundaries.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices described above may have application in conventional medical treatments and procedures conducted by a medical professional, as well as application in robotic-assisted medical treatments and procedures. By way of example only, various teachings herein may be readily incorporated into a robotic surgical system such as the DAVINCI™ system by Intuitive Surgical, Inc., of Sunnyvale, Calif. Similarly, those of ordinary skill in the art will recognize that various teachings herein may be readily combined with various teachings of U.S. Pat. No. 6,783,524, entitled "Robotic Surgical Tool with Ultrasound Cauterizing and Cutting Instrument," published Aug. 31, 2004, the disclosure of which is incorporated by reference herein.

Versions described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by an operator immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art.

For instance, the examples, embodiments, geometries, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. A surgical instrument, comprising:
    (a) a body;
    (b) a shaft assembly extending distally from the body and including an acoustic waveguide configured to couple with an ultrasonic transducer;
    (c) an end effector, including:
        (i) an ultrasonic blade in acoustic communication with the acoustic waveguide, and
        (ii) a clamp arm movably coupled relative to the ultrasonic blade and configured to move from an open position toward a closed position for compressing a tissue against the ultrasonic blade;
    (d) a clamp actuator movably coupled relative to the body and configured to selectively move from a first actuator position toward a second actuator position, wherein the clamp actuator is operatively coupled to the clamp arm to thereby direct movement of the clamp arm from the open position toward the closed position as the clamp actuator respectively moves from the first actuator position toward the second actuator position; and
    (e) a blade cooling system including a pressurized syringe, wherein the pressurized syringe includes a fluid reservoir configured to house a fluid coolant therein, wherein the pressurized syringe is operatively coupled with the clamp actuator and selectively operable to discharge the fluid coolant onto the ultrasonic blade in response to the clamp actuator moving from the second actuator position to the first actuator position, wherein the blade cooling system further includes:
        (i) a plunger positioned within the fluid reservoir and configured to selectively move therein for discharging the fluid coolant from the fluid reservoir, and
        (ii) a plug operatively connected to the plunger and configured to be selectively rotated to thereby direct the plunger to change a fluid pressure within the fluid reservoir.

2. The surgical instrument of claim 1, wherein the plug includes a threaded plug,
    wherein rotation of the threaded plug is operable to direct the plunger to change the fluid pressure within the fluid reservoir.

3. The surgical instrument of claim 2, the blade cooling system further including a compression spring positioned in contact with the plunger and the threaded plug is positioned in contact with the compression spring, wherein rotation of the threaded plug in a first rotational direction is operable to increase the fluid pressure within the fluid reservoir, wherein rotation of the threaded plug in a second rotational direction is operable to decrease the fluid pressure within the fluid reservoir.

4. The surgical instrument of claim 3, the threaded plug including a key accessible from an outer surface of the body, wherein the key is selectively operable to rotate the threaded plug.

5. The surgical instrument of claim 1, the clamp actuator further including a catch trigger and the blade cooling system further includes a valve, wherein the catch trigger is configured to open the valve upon the clamp actuator moving from the second actuator position to the first actuator position to thereby discharge the fluid coolant onto the ultrasonic blade.

6. The surgical instrument of claim 5, the valve further including a detent, wherein the catch trigger is configured to contact the detent to open the valve.

7. The surgical instrument of claim 5, the blade cooling system further including a torsion spring operatively coupled with the valve, wherein the torsion spring is configured to bias the valve in a closed position.

8. The surgical instrument of claim 1, the shaft assembly further including:
    (i) an inner tube,
    (ii) an outer tube, and
    (iii) an interior space between the inner tube and the outer tube, wherein the interior space is in fluid communication with the fluid reservoir and configured to receive the fluid coolant discharged from the fluid reservoir for communication toward the ultrasonic blade.

9. The surgical instrument of claim 8, the blade cooling system further including:
    (i) the plunger positioned within the fluid reservoir and configured to selectively move therein for discharging the fluid coolant from the fluid reservoir, and
    (ii) a fluid passageway fluidly connecting the fluid reservoir to the interior space of the shaft assembly, and wherein the plunger is operable to compress fluid coolant within the fluid reservoir thereby directing the fluid coolant through the fluid passageway.

10. The surgical instrument of claim 1, wherein the shaft assembly defines a longitudinal axis and further includes a knob operatively connected to the end effector, wherein the knob is configured to rotate about the longitudinal axis to thereby rotate the end effector about the longitudinal axis.

11. A surgical instrument, comprising:
    (a) a body;
    (b) a shaft assembly extending distally from the body and including an acoustic waveguide configured to couple with an ultrasonic transducer;
    (c) an end effector, including:
        (i) an ultrasonic blade in acoustic communication with the acoustic waveguide, and
        (ii) a clamp arm movably coupled relative to the ultrasonic blade and configured to move from an open position toward a closed position for compressing a tissue against the ultrasonic blade;
    (d) a clamp actuator movably coupled relative to the body and configured to selectively move from a first actuator position toward a second actuator position, wherein the clamp actuator is operatively coupled to the clamp arm to thereby direct movement of the clamp arm from the open position toward the closed position as the clamp actuator respectively moves from the first actuator position toward the second actuator position wherein the clamp actuator further includes a catch trigger; and
    (e) a blade cooling system, including:
        (i) a fluid reservoir configured to house a fluid coolant therein,
        (ii) a valve, wherein the valve biased in a closed position, wherein the valve is configured to momentarily transition to the open position to discharge the fluid coolant onto the ultrasonic blade in response to the clamp actuator moving from the second actuator position to the first actuator position,
        (iii) a detent,
    wherein the catch trigger is configured to contact the detent to open the valve upon the clamp actuator moving from the second actuator position to the first actuator position to thereby discharge the fluid coolant onto the ultrasonic blade.

12. The surgical instrument of claim 11, the blade cooling system further including a plunger positioned within the fluid reservoir and configured to selectively move therein for discharging the fluid coolant from the fluid reservoir.

13. The surgical instrument of claim 11, the blade cooling system further including a torsion spring operatively coupled with the valve, wherein the torsion spring is configured to bias the valve in a closed position.

14. The surgical instrument of claim 11, the shaft assembly further including:
   (i) an inner tube,
   (ii) an outer tube, and
   (iii) an interior space between the inner tube and the outer tube, wherein the interior space is in fluid communication with the fluid reservoir and configured to receive the fluid coolant discharged from the fluid reservoir for communication toward the ultrasonic blade.

15. The surgical instrument of claim 14, the blade cooling system further including:
   (i) a plunger positioned within the fluid reservoir and configured to selectively move therein for discharging the fluid coolant from the fluid reservoir, and
   (ii) a fluid passageway fluidly connecting the fluid reservoir to the interior space of the shaft assembly,
   wherein the plunger is operable to compress fluid coolant within the fluid reservoir thereby directing the fluid coolant through the fluid passageway.

16. A surgical instrument, comprising:
   (a) a body;
   (b) a shaft assembly extending distally from the body and including an acoustic waveguide configured to couple with an ultrasonic transducer;
   (c) an end effector, including:
      (i) an ultrasonic blade in acoustic communication with the acoustic waveguide, and
      (ii) a clamp arm movably coupled relative to the ultrasonic blade and configured to move from an open position toward a closed position for compressing a tissue against the ultrasonic blade;
   (d) a clamp actuator including an actuator portion and movably coupled relative to the body to direct movement of the clamp arm; and
   (e) a blade cooling system, including:
      (i) a fluid reservoir to house a fluid coolant therein,
      (ii) a plunger configured to pressurize the fluid reservoir, and
      (iii) a valve selectively operable to open to discharge the fluid coolant from the fluid reservoir onto the ultrasonic blade in response to the clamp actuator moving the clamp arm from the closed position to the open position,
   wherein the actuator portion is configured to contact the valve to open the valve in response to the clamp actuator moving the clamp arm from the closed position to the open position.

17. The surgical instrument of claim 16, the blade cooling system further including:
   (i) a compression spring positioned in contact with the plunger, and
   (ii) a threaded plug positioned in contact with the compression spring, wherein rotation of the threaded plug in a first rotational direction is operable to direct the plunger to increase a fluid pressure within the fluid reservoir, wherein rotation of the threaded plug in a second rotational direction is operable to direct the plunger to decrease the fluid pressure within the fluid reservoir.

18. The surgical instrument of claim 17, the threaded plug including a key accessible from an outer surface of the body, wherein the key is selectively operable to rotate the threaded plug.

19. The surgical instrument of claim 16, the actuator portion includes a catch trigger, wherein the valve further includes a detent, wherein the catch trigger is configured to contact the detent to open the valve in response to the clamp actuator moving the clamp arm from the closed position to the open position.

20. The surgical instrument of claim 16, wherein the actuator portion includes a catch trigger configured to contact the valve in response to the clamp actuator moving the clamp arm from the closed position to the open position.

* * * * *